(12) United States Patent
Abbott et al.

(10) Patent No.: US 9,012,569 B2
(45) Date of Patent: Apr. 21, 2015

(54) OIL EMULSIONS AND METHODS FOR MANUFACTURE AND USE THEREOF

(75) Inventors: Nicholas L. Abbott, Madison, WI (US); Francesco Caruso, Melbourne (AU); Jugal K. Gupta, Houston, TX (US); Sri Sivakumar, Kanpur (IN)

(73) Assignee: Wisconsin Alumni Research Foundation, Madison, WI (US)

( * ) Notice: Subject to any disclaimer, the term of this patent is extended or adjusted under 35 U.S.C. 154(b) by 1385 days.

(21) Appl. No.: 12/354,565

(22) Filed: Jan. 15, 2009

(65) Prior Publication Data

US 2009/0317792 A1 Dec. 24, 2009

Related U.S. Application Data

(60) Provisional application No. 61/021,235, filed on Jan. 15, 2008.

(51) Int. Cl.
- C08F 2/32 (2006.01)
- G01N 21/64 (2006.01)
- G01N 33/542 (2006.01)
- G01N 33/543 (2006.01)

(52) U.S. Cl.
CPC ...... *G01N 33/54373* (2013.01); *G01N 21/6428* (2013.01); *Y10S 514/938* (2013.01)

(58) Field of Classification Search
CPC .......... A61K 9/1635; A61K 47/48176; H01M 2300/0094; H01M 8/1053; G01N 33/54373; G01N 21/6428
See application file for complete search history.

(56) References Cited

U.S. PATENT DOCUMENTS 6,720,007 B2 * 4/2004 Walt et al. ............. 424/489

FOREIGN PATENT DOCUMENTS

| WO | 2007031345 A2 | 3/2007 |
| WO | 2007041570 A1 | 4/2007 |

OTHER PUBLICATIONS

Shenoy et al. Layer-by-layer engineering of miocompatible, decomposable core-shell structures. Biomacromolecules 2003, vol. 4, pp. 265-272.*

Kobayashi et al. Silicon array of elongated through-holes for monodisperse emulsion droplets. AIChE Journal 2002, vol. 48, No. 8, pp. 1639-1644.*

Sivakumar, S.; Gupta, J. K.; Abbott, N. L.; Caruso, F. Monodisperse emulsions through templating polyelectrolyte multilayer capsules. Chem. Mater. 2008, 20, 2063-2065.

Wang, Y. J.; Angelators A. S; Caruso F. Template synthesis of nanostructured materials via layer-by-layer assembly. Chem. Mater. 2008, 20, 848-858.

Jang, C. H.; Cheng, L. L.; Olsen, C. W.; Abbott, N. L. Anchoring of nematic liquid crystals on viruses with different envelope structures. Nano Lett. 2006, 6, 1053-1058.

Lockwood, N. A.; Cadwell, K. D.; Caruso, F.; Abbott, N. L. Formation of polyelectrolyte multilayer films at interfaces between thermotropic liquid crystals and aqueous phases. Adv. Mater. 2006, 18, 850-854.

(Continued)

*Primary Examiner* — Shafiqul Haq
(74) *Attorney, Agent, or Firm* — Quarles & Brady LLP

(57) ABSTRACT

The invention provides oil emulsion droplets and a general and facile method for providing same through the use of templating multilayer capsules. The oil emulsion droplets are further useful in fabricating liquid crystal droplet-based biosensors for the detection of target analytes such as bacteria or viruses in a sample.

10 Claims, 15 Drawing Sheets

(56) References Cited

OTHER PUBLICATIONS

Tjipto, E.; Cadwell, K. D.; Quinn, J. F.; Johnston, A. P. R.; Abbott, N. L.; Caruso, F. Tailoring the interfaces between nematic liquid crystal emulsions and aqueous phases via layer-by-layer assembly. Nano Lett. 2006, 6, 2243-2248.

Wang, Y. J.; Caruso, F. Template synthesis of stimuli-responsive nanoporous polymer-based spheres via sequential assembly. Chem. Mater. 2006, 18, 4089-4100.

Zelikin, A. N.; Li, Q.; Caruso, F. Degradable polyelectrolyte capsules filled with oligonucleotide sequences. Angew. Chem. Int. Ed. 2006, 45, 7743-7745.

Brake, J. M.; Daschner, M. K.; Abbott, N. L. Formation and characterization of phospholipid monolayers spontaneously assembled at interfaces between aqueous phases and thermotropic liquid crystals. Langmuir 2005, 21, 2218-2228.

Kim, E. B.; Lockwood, N.; Chopra, M.; Guzman, O.; Abbott, N. L.; de Pablo, J. J. Interactions of liquid crystal-forming molecules with phospholipid bilayers studied by molecular dynamics simulations. Biophys. J. 2005, 89, 3141-3158.

Tercero Espinoza, L. A.; Schumann, K. R.; Luk, Y. Y.; Israel, B. A.; Abbott, N. L. Orientational behavior of thermotropic liquid crystals on surfaces presenting electrostatically bound vesicular stomatitis virus. Langmuir 2004, 20, 2375-2385.

Brake, J. M.; Daschner, M. K.; Luk, Y. Y.; Abbott, N. L. Biomolecular interactions at phospholipid-decorated surfaces of liquid crystals. Science 2003, 302, 2094-2097.

PCT Search Report PCT/US2009/031105.

E. Tjipto et al. "Tailoring the Interfaces between Nematic Liquid Crystal Emulsions and Aqueous Phases via Layer-by-Layer Assembly," Nanoletters, vol. 6, No. 10, 2006, pp. 2243-2248.

Zoldesi et al., "Encapsulation of emulsion dropletsby organo-silica shells," Journal of Colloid and Interface Science, vol. 308, No. 1, 2007, pp. 121-129.

Xu et al., "Generation of monodisperse particles by using microfluidics: Control over size, shape, and composition," Angewandte Chemie., vol. 44, No. 5, 2005, pp. 724-728.

Fernandez-Nieves et al., "Optically Anisotropic Colloids of Controllable Shape," Advanced Materials, vol. 17, No. 6, 2005, pp. 680-684.

Umbanhowar et al., "Monodisperse Emulsion Generation via Drop Break Off in a Coflowing System," Langmuir, vol. 16, 1999, pp. 347-351.

Hsu et al., "Rotational diffusion of Monodisperse Liquid Crystal Droplets," Journal of Colloid and Interface Science, vol. 200, 1998, pp. 182-184.

Bai et al., "A versatile bottom-up assembly approach to colloidal spheres from nanocrystals," Angewandte Chemie., vol. 46, No. 35, 2007, pp. 6770-6773.

Zoldesi et al., "Synthesis of Monodisperse colloidal Spheres, Capsules and Microballoons by Emulsion Templating," Advanced Materials, vol. 17, No. 7, 2005, pp. 924-928.

Caruso et al., "Nanoengineering of Inorganic and Hybrid Hollow spheres by Colloida," Science, vol. 282, 1998, pp. 1111-1114.

Donath et al., "Novel Hollow Polymer Shells by colloid-Templated Assembly of Polyelectrolytes," Angew. Chemie Int. Ed., vol. 37, No. 16, 1998, 2201-2205.

\* cited by examiner

| 0.0m | 0.2m | 0.4m | 0.6m | 0.8m | 1.0m |

9,012,569 B2

OIL EMULSIONS AND METHODS FOR MANUFACTURE AND USE THEREOF

CROSS-REFERENCE TO RELATED APPLICATIONS

This application claims the benefit of U.S. Provisional Application No. 61/021,235, filed Jan. 15, 2008, which is incorporated herein by reference in its entirety.

STATEMENT REGARDING FEDERALLY SPONSORED RESEARCH OR DEVELOPMENT

The present invention was made with government support from the National Science Foundation (Grant No. DMR-0602570) and the United States Army Research Office (Grant No. W911NF-06-1-0314). The United States Government has certain rights in the invention.

FIELD OF THE INVENTION

The invention relates generally to the field of emulsion engineering. More particularly, the present invention is directed to oil emulsions with pre-determined sizes and methods for providing such materials.

BACKGROUND OF THE INVENTION

General and facile methods that permit precise control over the size and surface chemistry of micrometer-scale oil droplets broadly enable both fundamental studies of confined condensed phases (e.g., effects of confinement on order) as well as advance a range of promising technologies that revolve around control of dispersed phases (e.g., nano-materials, meso-materials, responsive materials, optical materials, filters, sensors, and opto-electronic technologies).

Previous studies have shown that emulsion droplets can be prepared by various techniques, such as photopolymerization, ultrasonication, shearing of droplets and subsequent crystallization fractionation, droplet break-off in a co-flowing stream (microfluidics), and dispersion polymerization. Although most of these approaches result in polydisperse emulsions, emulsion droplets with limited control over interfacial properties, or the formation of polymerized droplets, the microfluidic approach enables the preparation of monodisperse emulsion droplets with sizes larger than approximately 2 μm. Typical quantities of emulsion droplets prepared by microfluidics are on the order of 1-5 $s^{-1}$ for a single junction. Recent, more elaborate multiple-device systems can produce 100-1000 particles $s^{-1}$.

Liquid crystal (LC) materials are emerging as promising candidates for a range of sensing and interfacial applications. The ordering of LCs is highly sensitive to molecular-level events at the LC interface, enabling such interactions to be coupled to the orientational order of LCs, and thus leading to changes in the optical properties of the LC. For example, LCs respond to and amplify small changes in temperature, shear, electric or magnetic fields, or the structure of solid surfaces with which they are in contact. This qualifies LCs as "molecular magnifying glasses", allowing events that occur at the nanoscale level to be observed at the spatial scale of the naked eye (and far-field optics) without the need for additional instrumentation. Recent reports have demonstrated that it is also possible to tailor the interfaces of LCs at aqueous interfaces in ways that provide control over the orientational order of the LC. For example, recent studies on thin films of supported LCs have demonstrated that orientational ordering transitions in LCs can be triggered by the presence of lipids, surfactants, proteins, and viruses. These changes in orientational order arise in part from coupling between the aliphatic tails of the adsorbed amphiphiles and the mesogens of the LC, and the nature and extent of these changes is influenced by the structure of the amphiphiles (e.g., tail length or head group structure) or by chemical or physical events in the aqueous phase that disrupt or perturb these assemblies (such as the binding or enzymatic action of a protein). Additionally, LC-based reporting offers potential advantages over conventional techniques because it does not require complex instrumentation or labels (enzymatic or fluorescent).

Despite these advances, there is a need for a general and scalable, highly parallel synthesis strategy that permits the formation of emulsions with fine control over their size (even below 1 μm) and surface chemistry. The manufacture of such emulsions would provide a route to new sensing and interfacial technologies, particularly biosensors based on monodisperse LC droplet emulsions.

SUMMARY OF THE INVENTION

Here, the inventors demonstrate a versatile method for a general and scalable, highly parallel synthesis strategy that permits the formation of emulsions with pre-determined sizes. The method is based on templating multilayer capsules formed by the layer-by-layer (LbL) adsorption of macromolecular assembly materials on sacrificial particles to produce a range of emulsions of predetermined size and surface chemistry.

Accordingly, the present invention encompasses a method for providing oil emulsion droplets. Such a method includes steps of: (a) preparing templating multilayer capsules by: (i) layer-by-layer (LbL) coating of sacrificial particles with macromolecular assembly materials to yield multilayer-coated sacrificial particles; and (ii) etching the multilayer-coated sacrificial particles to remove the sacrificial particle thereby yielding the templating multilayer capsules; (b) infiltrating the templating multilayer capsules with oil to provide multilayer-coated oil droplets; and (c) disassembling the multilayer-coating of the multilayer-coated oil droplets to provide oil emulsion droplets.

In certain embodiments, the macromolecular assembly materials include at least one polycation and one polyanion that yield multilayer-coated sacrificial particles having alternating layers or complexes of said polycation and polyanion in the LbL coating step. In yet other embodiments, the macromolecular assembly materials include at least two non-ionic polymers that that yield multilayer-coated sacrificial particles having alternating layers of the non-ionic polymers in the LbL coating step. In yet other embodiments, the macromoleular assembly materials can include chemically reactive groups that lead to formation of covalent bonds within the capsules formed around the sacrificial particles. In yet other embodiments, the macromolecular assembly formed on the surface of the sacrificial particle is comprised of a single type of macromolecular species. In one aspect of such embodiments, the single type of macromolecular assembly material can yield multilayer coated sacrificial particles through sequential covalent reactions leading to deposition of the multilayer. The term multilayer assembly is used herein to include assemblies made from both a single type of macromolecular species and multiple types of macromolecular species.

The method is robust in its application and is generally adapted to provide oil emulsion droplets of mineral, vegetable, and synthetic substances and animal and vegetable fats. Particularly preferred materials to form oil emulsion droplets according to the invention include, for example, silicone oil, a paraffin oil, a liquid crystal, a vegetable oil, a perfluorinated oil, a reactive oil, or a polymerizable oil.

As well, the method facilitates the production of monodisperse oil emulsion droplets and templating multilayer capsules of pre-determined size, including droplet and capsule diameters between about 10 nm to about 10 mm. In certain embodiments, the oil emulsion droplets are monodisperse and have a granulomeric distribution of about 10% or less. In certain preferred embodiments, monodisperse liquid crystal oil emulsion droplets are produced, preferably having a uniform pre-determined diameter from about 0.1 μm to about 10 μm. In other embodiments, the monodisperse liquid crystal emulsion droplets preferably have a granulomeric distribution of about 30% or less, more preferably a granulomeric distribution of about 20% or less, and most preferably a granulomeric distribution of about 10% or less.

Sacrificial particles useful in the present method are generally any organic or inorganic particle having a defined size and shape that can be obtained in a controlled size range and selectively etched to provide LbL-coated template capsules. Sacrificial particles can be made of, but are not limited to, metals, inorganic oxides, ceramics, salt crystals, polymers, carbon nanomaterials, eukaryotic and prokaryotic organisms, virus particles, lipid vesicles, protein assemblies, and polysaccharide assemblies. Examples of specific useful materials include, but are not limited to, particles of polystyrene, melamine formaldehyde, silica, gold, liquid crystal, nickel, carbon microfiber, calcium carbonate, and cells (e.g., yeast cells). Sacrificial particles may be spherical or non-spherical in their shape and therefore the shape of multilayer-coated capsules formed there from may be controlled by the artisan.

In another aspect, the present invention provides a method for providing multilayer-coated oil emulsion droplets. Such materials are particularly useful in sensor and opto-electronic technologies where the functionalization of oil droplet surfaces is advantageous. Accordingly, a method of providing multilayer-coated oil emulsion droplets includes steps of: (a) preparing templating multilayer capsules by: (i) layer-by-layer (LbL) coating of sacrificial particles with macromolecular assembly materials to yield multilayer-coated sacrificial particles; and (ii) etching the multilayer-coated sacrificial particles to remove the sacrificial particle thereby yielding the templating multilayer capsules; and (b) infiltrating the templating multilayer capsules with oil to provide multilayer-coated oil emulsion droplets.

In addition to allowing the functionalization of oil droplets' surfaces, the present method also allows multilayer-coated oil emulsion droplets to be based on non-spherical sacrificial particles and, therefore, the shape of the resulting oil droplet may be a variety of predetermined non-spherical shapes. In addition, spherical or non-spherical multilayer-coated oil emulsion droplets may be provided in the form of aggregated assemblies of two or more multilayer-coated oil emulsion droplets. In preferred embodiments of this method, the multilayer-coated oil emulsion droplets have a granulomeric distribution of about 30% or less, more preferably a granulomeric distribution of about 20% or less, and most preferably a granulomeric distribution of about 10% or less. In other embodiments of this method, the multilayer-coated oil emulsion droplets are polyelectrolyte multilayer-coated oil emulsion droplets of a predetermined size, and are preferably polyelectrolyte multilayer-coated liquid crystal emulsion droplets, more preferably having a diameter of about 0.1 μm to about 10 μm. Preferably, the polyelectrolyte multilayer-coated liquid crystal emulsion droplets have a granulomeric distribution of about 10% or less. In one alternative embodiment of the method, the multilayer-coated oil emulsion droplets are less than 100% filled with oil. In another embodiment, the multilayer coating of the multilayer-coated oil emulsion droplets contains a macromolecular assembly material that can undergo a subsequent covalent reaction.

Of course, the invention further encompasses the oil emulsion droplets and multilayer-coated oil emulsion droplets prepared by the methods described and claimed herein. Accordingly, in one aspect, the invention provides an oil emulsion comprising monodisperse oil emulsion droplets having a uniform predetermined diameter from about 10 nm to about 10 mm. Such monodisperse oil emulsion droplets preferably have a granulomeric distribution of about 30% or less, more preferably, of about 20% or less, and most preferably about 10% or less. In another aspect, the oil emulsion droplets are multilayer-coated monodisperse oil emulsion droplets, which may be less than 100% filled with oil.

In certain preferred embodiments, the monodisperse oil emulsion droplets are monodisperse liquid crystal emulsion droplets, preferably having a uniform predetermined diameter of about 0.1 μm to about 10 μm and, yet more preferably, having a granulomeric distribution of about 30% or less. In a preferred aspect of this embodiment, the oil emulsion droplets have a granulomeric distribution of about 20% or less. In a more preferred aspect of this embodiment, the oil emulsion droplets have a granulomeric distribution of about 10% or less. In certain embodiments, the monodisperse liquid crystal emulsion droplets further comprise an enzymatic substrate or, alternatively, an amphiphile.

The invention has several advantages over previous technologies, including microfluidic-based approaches. These include: (i) the ability to readily prepare monodisperse droplets of over a wide range of sizes, as capsule templates can be prepared with diameters as small as nanometers and as large as millimeters; (ii) the preparation of large quantities of emulsion droplets, as the templating method is parallel and scalable; and (iii) the preparation of emulsion droplets of different composition with well-defined surface functionality.

Based upon the droplets manufactured by the methods described and claimed herein, the invention further provides a liquid crystal-based method for detecting a target analyte in a sample. Such a method includes steps of: (a) contacting a sample with a liquid crystal droplet; and (b) detecting a change of orientation of liquid crystal contained within the liquid crystal droplet wherein the change of orientation corresponds to the presence of a target analyte contained within the sample.

In certain embodiments, the target analyte detected in the method is a bacterium, a virus, a lipid, or a chemical species. The liquid crystal droplet used in the method preferably has a predetermined diameter from about 0.1 μm to about 10 μm and, furthermore, a plurality of droplets utilized in the method, as is the preferred technique, preferably have a granulomeric distribution of about 30% or less. In a more preferred aspect, the oil emulsion droplets have a granulomeric distribution of about 20% or less, most preferably, 10% or less.

In yet another aspect, the invention provides a liquid crystal-based method of detecting an enzymatic activity. Such a method includes steps of: (a) contacting an enzyme with a liquid crystal droplet of a predetermined size decorated with a substrate of the enzyme; and (b) detecting a change of orientation of liquid crystal contained within the liquid crystal droplet of a predetermined size wherein the change of orientation corresponds to the enzyme exhibiting enzymatic activity toward the substrate.

Based upon the materials and methods described and claimed herein, the invention further encompasses a liquid crystal-based sensor for detecting a target analyte in a sample. Such a sensor includes: (a) an emulsion including liquid crystal droplets; and (b) a detector capable of detecting and reporting a change in orientation of liquid crystal contained in the liquid crystal droplets in response to the liquid crystal droplets contacting a target analyte contained in a sample.

The liquid crystal droplets utilized in the sensor preferably have a uniform predetermined diameter from about 0.1 μm to about 10 μm and, yet more preferably, have a granulomeric distribution of about 10% or less.

Other objects, features and advantages of the present invention will become apparent after review of the specification, claims and drawings.

DETAILED DESCRIPTION OF THE INVENTION

I. In General

Figure 1:
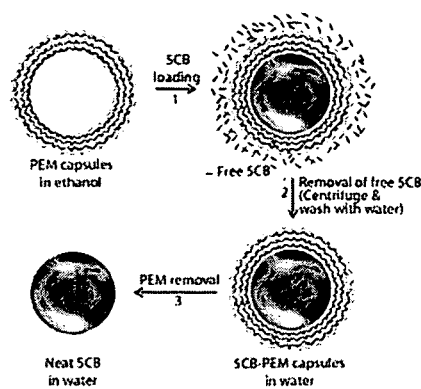
FIG. 1. Schematic representation of the procedure used to prepare monodisperse emulsion droplets. The inset within the sketch of the capsules is a polarized light micrograph of a 5CB droplet.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed nonprovisional applications.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. Definitions

As used herein, the term "monodisperse", when used in the context of oil emulsion droplets, refers to emulsions wherein the droplets are of very similar size, i.e., wherein the granulometric distribution of the dispersed phase droplets is very narrow, such as less than or equal to 30%, more preferably less than 20%, most preferably less than 10%.

The term "capsule" means an encompassing structure or small container that is spherical or non-spherical in shape.

The term "layer-by-layer" or "LbL" coating means the sequential adsorption of macromolecular assembly materials onto a surface to form a multilayer coating or complex on a surface. The macromolecular assembly materials that are sequentially adsorbed may be a single type of macromolecular assembly species or may be alternating types of macromolecular assembly species. It is understood by those skilled in the art that the macromolecular assembly materials may reorganized during or after layer-by-layer deposition, and that layered structured do not necessarily result from layer-by-layer deposition processes. Suitable macromolecular assembly materials include, for example, charged polymers (i.e., polyelectrolytes), pairs of oppositely charged polymers, non-ionic polymers capable of forming hydrogen bonded macromolecular assemblies, or polymers including reactive chemical moieties that undergo covalent linkage to form covalently-linked macromolecular assemblies.

The term "multilayer coating" means the surface formed in the layer-by layer sequential adsorption process. Such coatings may be prepared by the assembly of a single type or multiple types of polymer or macromolecular assembly species. The term is not used to mean a particular state of ordering of the surface, as multilayer coatings may have one or more layers, or they may not have any layered ordering of the deposited materials.

The term "sacrificial particles" refers to any organic or inorganic particles having a defined shape and size that can be obtained in a controlled size range upon which layer-by-layer coating may be carried out to yield LbL-coated sacrificial particles. Such resultant LbL-coated sacrificial particles should then be suitable to undergo subsequent etching to remove, erode, or dissolve the sacrificial particle and yield LbL-coated template capsules. Sacrificial particles may be based on a wide range of materials including, but not limited to, metals, inorganic oxides, ceramics, salt crystals, polymers, carbon nanomaterials including carbon nanotubes and microfabricated particles with shapes defined by molds from which the particles are formed, and biological-based materials including eukaryotic and prokaryotic organisms, virus particles, lipid vesicles, protein assemblies, and polysaccharide assemblies. Preferred materials for sacrificial particles include, e.g., polystyrene, melamine formaldehyde, silica, gold, liquid crystal, nickel, carbon microfiber, calcium carbonate, and eukaryotic or prokaryotic cells (e.g., yeast cells).

The term "etching" refers to the erosion of the sacrificial particle contained in an LbL-coated sacrificial particle as a way to provide LbL-coated template capsules. The specific type of etching to be carried out will depend upon the composition of the sacrificial particle. Etching can be carried out by exposing LbL-coated sacrificial particles to a solvent. The solvent is selected for its ability to erode the sacrificial particle without significant disruption of the multilayer coating. To illustrate, exemplary materials for sacrificial particles are listed below with their corresponding etching solvents provided in parentheses: polystyrene (toluene, tetrahydrofuran), melamine formaldehyde (acidic aqueous solution of less than pH 1.5), silica (hydrofluouric acid), gold (potassium cyanide), liquid crystal, (ethanol) nickel (hydrochloric acid), carbon microfiber (calcination), calcium carbonate (ethylenediaminetetra-acetic acid at pH of 7.5), or cells, such as yeast cells (deproteinizer, such as NaOCl).

The term "multilayer capsules" refers to either (1) capsules prepared by the sequential assembly of a single type of macromolecular assembly material (see i.e. assembly using covalent reaction "click chemistry" as disclosed by Caruso et al., Journal of the American Chemical Society, 128 (29), 9318-9319), or (2) capsules having at least one "bilayer" of two different macromolecular assembly materials, as provided by the LbL process. The term "bilayer", as used herein, shall refer to the accumulated layers of material deposited on a surface as a result of having passed through at least one complete cycle of the general layer-by-layer methodologies described below and schematically shown in the figures.

The term "polyelectrolyte" means a polymeric substance, either natural (e.g., protein, nucleic acid, or carbohydrate) or synthetic (e.g., poly(allylamine hydrochloride or poly(acrylic acid)), containing ionic or partially charged constituents being either cationic or anionic.

The term "polyelectrolyte multilayer (PEM) capsules" refers to either capsules having at least one "bilayer" of deposited polyanion and polycation or capsules containing a single type of adsorbed polycation or polyanion.

Use of the term "bilayer" herein is not intended to place a restriction on the types of structures that are formed as a result of having passed through at least one complete cycle of the general methodologies described below and schematically shown in the figures and described in this disclosure. The term "bilayer" shall refer to the sequential exposure of the interface to separate solutions of materials to be deposited in alternating fashion. Regarding certain PEM-related embodiments, it is widely understood by those skilled in the art that the sequential exposure of an interface to polyelectrolytes of opposite charge can lead to a range of interfacial structures and that in some cases there is substantial mixing of the PEM with the polyelectrolyte in solution to which the PEM is exposed. In some cases, the growth of the PEM occurs linearly with the number of cycles of exposure, in other cases so-called exponential growth regimes are observed. Preferred embodiments utilize capsules having at least two bilayers of alternating materials, more preferably more than four bilayers, although specific applications will dictate the optimum number of bilayers to be determined by no more than routine experimentation.

The term "oil" generally refers to any of numerous mineral, vegetable, and synthetic substances and animal and vegetable fats that are generally slippery, viscous, liquid or liquefiable at room temperatures, soluble in various organic solvents such as ether but not in water. The present method may be practiced with a wide variety of oils including, but not limited to, silicone oils, paraffin oils, liquid crystals, perfluorcarbon oils, vegetable oils, or polymerizable oils. Liquid crystal is a particularly preferred material due to the wide utility of liquid crystal in sensor and opto-electronic applications. As can be appreciated, an oil should not destroy the multilayer-coated capsule in which it is encased during present template-based methods of providing oil emulsion or multilayer-coated oil emulsion droplets.

By "liquid crystal" we mean an organic composition in an intermediate or mesomorphic state between solid and liquid. Suitable liquid crystals for use in the present invention include, but are not limited to, thermotropic, polymeric, lyotropic, chromonic, smectic, nematic, ferroelectric and cholesteric liquid crystals. Suitable liquid crystals may range widely in molecular weight and may be low molecular weight (i.e., less than 1000 Da), high molecular weight (i.e., greater than 1000 Da), or mixtures of the two.

The term "disassembled" refers to the removal of the multilayer-coating of multilayer-coated oil emulsion droplets to yield oil emulsion droplets. Disassembly results in substantially naked oil emulsion droplets. However, the invention further contemplates alternative embodiments in which partially-multilayer coated oil emulsion droplets are generated, having a degree of disassembly from about 1 to about 99%.

III. The Invention

Herein, the inventors describe a versatile method for a general and scalable, highly parallel synthesis strategy that permits the formation of emulsions with pre-determined sizes. The method is based on templating multilayer capsules formed by the layer-by-layer (LbL) adsorption of macromolecular assembly materials on sacrificial particles, to produce a range of emulsions of a predetermined size and surface chemistry.

More particularly, the method comprises preparing templating multilayer capsules by layer-by-layer coating of sacrificial particles with polyelectrolytes to yield multilayer-coated sacrificial particles and etching the multilayer-coated sacrificial particles to remove the sacrificial particles, thereby yielding the templating multilayer capsules. FIG. 1 depicts an exemplary templating polyelectrolyte multilayer (PEM) capsule undergoing loading with an exemplary oil, in this case, the liquid crystal 5CB. The liquid crystal infiltrates the PEM coating and substantially fills the capsule's internal cavity. Free liquid crystal is then removed by, in this case, rounds of washing and centrifugation, to yield purified monodisperse PEM-coated oil droplets. The PEM-coating of the monodisperse PEM-coated oil droplets is then disassembled to provide monodisperse oil emulsion droplets of pre-determined size.

Accordingly, the present invention encompasses a method for providing oil emulsion droplets. Such a method includes steps of: (a) preparing templating multilayer capsules by: (i) layer-by-layer (LbL) coating of sacrificial particles with macromolecular assembly materials to yield multilayer-coated sacrificial particles; and (ii) etching the multilayer-coated sacrificial particles to remove the sacrificial particle thereby yielding the templating multilayer capsules; (b) infiltrating the templating multilayer capsules with oil to provide multilayer-coated oil droplets; and (c) disassembling the multilayer-coating of the multilayer-coated oil droplets to provide oil emulsion droplets. This method can provide oil emulsion droplets with either a single type or multiple types of macromolecular assembly materials on the surface of the oil droplet.

In another aspect, the present invention provides a method for providing multilayer-coated oil droplets, stopping short of generating naked oil emulsion droplets. Multilayer-coated oil droplets provided by such methods are particularly useful in sensor and opto-electronic technologies where functionalized oil droplet surfaces offer advantages. Accordingly, a method of providing multilayer-coated oil emulsion droplets includes steps of: (a) preparing templating multilayer capsules by: (i) layer-by-layer (LbL) coating of sacrificial particles with macromolecular assembly materials to yield multilayer-coated sacrificial particles; and (ii) etching the multilayer-coated sacrificial particles to remove the sacrificial particle thereby yielding the templating multilayer capsules; and (b) infiltrating the templating multilayer capsules with oil to provide multilayer-coated oil emulsion droplets. Such methods allow for the production of oil droplets functionalized with a variety of coatings that can be tailored to specific applications. While spherical multilayer-coated oil emulsion droplets are provided by the invention, alternative methods contemplated by the invention include methods for producing multilayer-coated oil emulsion droplets of non-spherical shape and/or in the form of aggregated assemblies of two or more multilayer-coated oil emulsion droplets.

The layer-by-layer (LbL) assembly technique used herein comprises the sequential adsorption of various macromolecular assembly materials onto surfaces. For instance, polyelectrolyte multilayer (PEM) films may be formed by alternately immersing the surface of a solid into solutions of polycations or polyanions. In this example, the LbL process begins with the adsorption of a charged species onto a substrate of opposite charge, thereby reversing the substrate surface charge. Further layers are then deposited by the alternate adsorption of oppositely charged species onto the substrate, until the desired thickness is achieved. The versatility of the LbL approach has allowed a broad range of materials (e.g., polymers, nanoparticles, lipids, proteins, dye molecules) to be assembled on various substrates, on the basis of not only electrostatic interactions but also hydrogen bonding, hydrophobic interactions, covalent bonding, and complementary base pairing. General LbL methodology and polyelectrolytes useful in such methods have been described previously, including in U.S. patent application Ser. No. 11/483,891 to Abbott et al., filed Jul. 10, 2006, which is hereby incorporated by reference herein.

The properties of multilayer-coated capsules or films, such as composition, thickness, and function, can be readily tuned by varying the type of species adsorbed, the number of layers deposited, and the conditions employed during the assembly process. Removal of the templating substrate following LbL formation can give rise to free-standing nanostructured materials with different morphologies and functions.

Polyelectrolytes that can be used in the present invention include, but are not limited to, synthetic, linear polyelectrolytes; dendrimers; side-chain polyelectrolytes, branched polyelectrolytes, charged biomolecules such as polynucleotides, proteins and polysaccharides; or polyvalent small molecular weight organic compounds. Exemplary polycations and polyanions useful in the formation of PEM capsules according to the invention include, but are not limited to the following polymers to which ionic groups are covalently attached: polystyrenes, polyamines, polyesters, non-biodegradable polyurethanes, polyureas, poly(ethylene vinyl acetate), polypropylene, polymethacrylate, polyethylene, polycarbonates, and poly(ethylene oxide)s. A preferred combination of polyelectrolytes for use in the invention are poly(sodium-4-styrenesulfonate) (PSS) and poly(allylamine hydrochloride) (PAH).

Non-ionic polymers may also be utilized in LbL formation to give rise to suitable multiplayer template capsules for use in the invention. It is understood in the art that bilayers can be formed by sequential contact of an interface to non-ionic polymers. In these situations, a variety of interactions such as, but not limited to, van der Waals interactions, hydrogen bonding, acid-based interactions, and metal ion-ligand coordination interactions can facilitate formation of the bilayers. Furthermore, sequential contact with nanoparticles can also lead to bilayer formation. In certain embodiments, non-ionic polymers possess partial charges due to differential electronegativities of the atoms comprising the respective molecules. An exemplary combination of non-ionic polymers capable of forming a hydrogen-bonded multilayer via the LbL approach is poly(methacrylic acid) (PMA) and poly(vinylpyrrolidone) (PVPON).

Degradable polymers such as polylactic acid and polyglycolic acid may also be used in the present invention. The polymers can also include naturally occurring components of the extracellular matrix of cells (e.g., laminin and collagens) or synthetic polymers that incorporate peptides found in these naturally occurring polypeptides. The materials can also be peptide or synthetic substrates for enzymes such as proteinases and proteases. The process of multilayer formation and the physical properties of the resulting capsules (e.g., morphology, thickness, layer interpenetration) depend on the deposition procedure, the chemical structure and molecular weight of the polyelectrolytes, and the ionic strength and pH of the deposition solution.

The present method may be practiced with a wide variety of oils including, numerous mineral, vegetable, and synthetic substances and animal and vegetable fats. Particularly advantageous oils include, but are not limited to, silicone oil, a paraffin oil, a liquid crystal, a vegetable oil, a perfluorinated oil, a reactive oil, or a polymerizable oil. Liquid crystal is a particularly preferred material for use in the invention due to the wide utility of liquid crystal in sensor, opto-electronic, food science, personal healthcare, cosmetic and pharmaceutical applications. As can be appreciated, an oil should be selected that does not destroy the multilayer-coated capsule in which it is encased during present template-based methods of providing oil emulsion or multilayer-coated oil emulsion droplets.

Various liquid crystals (LCs) may be employed in liquid crystal-related aspects of the present invention. Examples of suitable liquid crystals, include, but are not limited to, 4-cyano-4'-pentylbiphenyl (5 CB), 7 CB, and 8 CB. A large listing of suitable liquid crystals is presented in "Handbook of Liquid Crystal Research" by Peter J. Collings and Jay S. Patel, Oxford University Press, 1997, ISBN 0-19-508442-X. Polymeric liquid crystals are also suitable for use in the methods of the present invention. Because the certain methods of the present invention include contacting the liquid crystal with aqueous solutions, preferred liquid crystals employed in those methods should be insoluble in water or have very limited solubility in water. Additionally, preferred liquid crystals employed in the invention should not react with water.

In the exemplary method described below, the liquid crystal is 4-cyano-4'-pentylbiphenyl (5 CB). Although various types of liquid crystal may be employed, nematic and thermotropic liquid crystals are preferred. However, smectic liquid crystals formed from 8 CB are also suitable for use in the present invention. Suitable liquid crystals further include smectic C, smectic C*, blue phases, cholesteric phases, smectic A, and polymeric liquid crystals.

In order to further illustrate the invention, the inventors provide the following non-limiting example of monodisperse emulsion droplet preparation using the thermotropic LC 5CB. The inventors focused on results obtained with 5CB because the birefringent properties of 5CB provide the basis of a simple means (polarized light microscopy) to determine the uptake of the oils into the capsules. It should be noted that the inventors carried out the preparation of monodisperse oil emulsions using, in addition to liquid crystal, silicone oil and paraffin oil. Detailed description of respective silicone oil and paraffin oil-related processes is provided in the following Examples section.

Both non-porous and mesoporous silica particles (with 2-3 nm and 10-40 nm pores)[23,24] were used as sacrificial particle templates. The silica particles (5±0.5 μm) were first amine-functionalized by grafting 3-aminopropyltriethoxysilane (APTS) to the particle surface. The APTS-functionalized silica particles were next coated with PEMs, and the coated particles were exposed to hydrofluoric acid (HF) to etch the silica core, resulting in the formation of hollow PEM capsules. Two types of polyelectrolyte capsules were investigated: electrostatically coupled poly(sodium-4-styrene-sulfonate) (PSS) and poly(allylamine hydrochloride) (PAH); and hydrogen-bonded poly(methacrylic acid) (PMA) and poly(vinylpyrrolidone) (PVPON).

These PEMs have been well-studied and were chosen because the PSS/PAH capsules are highly stable under different conditions, whereas the PMA/PVPON capsules can be readily disassembled due to weakening of the hydrogen bonding between the layers by changing the pH. APTS-functionalized silica is positively charged; hence, the anionic PE (PSS or PMA) was deposited as the first layer, followed by either PAH or PVPON as the second layer.

After etching of the silica cores with HF, the capsules were washed five times with water and twice with ethanol, 5CB was infiltrated through the semipermeable walls of the PEM capsules, and excess 5CB was removed from outside of the PEM capsules by contacting the capsules with water. This procedure resulted in formation of monodisperse PEM-coated oil droplets (denoted as oil-(PSS/PAH)$_4$ or oil-(PMA/PVPON)$_4$). Naked oil emulsion droplets were prepared by disassembling the PMA/PVPON layers upon exposure to pH 7.5 solutions.

Figure 2:
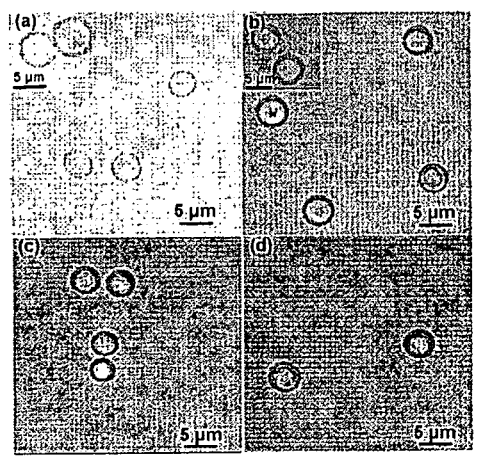
FIG. 2. Bright field optical micrographs of: (a) empty (PSS/PAH)$_4$ capsules made using MS templates (inset-empty (PSS/PAH)$_4$ capsules prepared from non-porous silica templates); (b) 5CB-filled (PSS/PAH)$_4$ capsules prepared from MS templates (inset-5CB-filled (PSS/PAH)$_4$ capsules made from non-porous silica templates); (c) silicone oil-filled (PSS/PAH)$_4$ capsules made from MS templates; and (d) paraffin oil-filled (PSS/PAH)$_4$ capsule prepared from MS templates.
Figure 3:
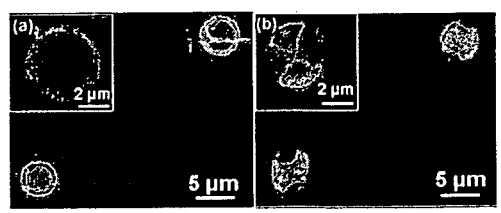
FIG. 3. (a) Fluorescence image of 5CB-filled (PSS/PAH-FITC)$_4$ capsules made from non-porous silica templates (inset is CLSM image of 5CB-filled (PSS/PAH-FITC)$_4$ capsules made from MS templates). (b) Polarized light micrographs (crossed polars) of 5CB-filled (PSS/PAH)$_4$ capsules made from non-porous silica templates (inset is polarized light micrograph of 5CB-filled (PSS/PAH)$_4$ capsules made from MS templates).

FIG. 2 shows a bright field optical micrograph of empty (PSS/PAH)$_4$ capsules prepared from mesoporous (MS) silica particles (FIG. 2a) and the same capsules after 5CB loading (FIG. 2b). The interference colors and optical contrast between the capsules and surrounding aqueous solution indicate that the (PSS/PAH)$_4$ capsules were filled with 5CB. Moreover, unlike empty (PSS/PAH)$_4$ capsules, the 5CB-loaded (PSS/PAH)$_4$ capsules did not collapse after drying (see FIG. 3), confirming the presence of 5CB in the capsules.

Similar results were obtained for capsules prepared from non-porous silica (inset in FIG. 2b). Optical micrographs of 5CB-filled capsules prepared from the non-porous and MS silica particles were indistinguishable. The same method was used to generate monodisperse silicone oil and paraffin oil droplets (FIGS. 2c and 2d), demonstrating the versatility of this technique.

Sizing of the oil-filled PEM capsules from microscopy images yielded diameters of 4.7±0.5 μm. There is minimal shrinkage in the size of oil-filled PEM capsules compared to the silica template used (5.0±0.5 μm). This is consistent with a report by Bruening and coworkers, where a 5% reduction in thickness was observed for PSS/PAH PEMs exposed to ethanol.

The inventors performed fluorescence microscopy studies to investigate whether or not PEs from the capsule wall infiltrate into the 5CB cores in the oil-filled capsules. Fluorescently-labeled PAH (FITC-PAH) was used instead of PAH to form the PEMs. A fluorescence image of 5CB-loaded (PSS/FITC-PAH)$_4$ capsules (made from non-porous silica particles) in water is shown in FIG. 2a. Uniform and ring-only fluorescence was observed for the 5CB-filled capsules, prepared either from the non-porous or MS spheres. Confocal laser scanning microscopy (CLSM) examination of 5CB-filled (PSS/FITC-PAH)$_4$ capsules made from MS (inset in FIG. 3a) also showed a well-defined ring fluorescence of the capsule wall. Further, control experiments with FITC-PSS as the first layer (data not shown) showed similar ring fluorescence, demonstrating that both of the PEs present in the capsule wall did not infiltrate into the interior of the 5CB-filled capsules. Polarized light microscopy was used to confirm the infiltration of the LC into the capsules. A polarized light micrograph (crossed polars) of 5CB-loaded (PSS/PAH)$_4$ capsules made from non-porous silica is shown in FIG. 3b, proving that the (PSS/PAH)$_4$ capsules were filled with 5CB. The micrograph also reveals that the 5CB droplets have a bipolar configuration, with each droplet containing two point defects (boojums) at the interface. Similarly, the LCs within 5CB-loaded PSS/PAH capsules made from MS also show the bipolar configuration (inset in FIG. 3b). This further indicates that the properties of the LCs within (PSS/PAH)$_4$ capsules made from MS and non-porous silica are similar. The inventors used polarized light microscopy to confirm that the 5CB filled 1, 3, 5, 8 and 10 μm (PSS/PAH)$_4$ capsules.

While no particular mechanism or mode of operation is adopted herein, the process of encapsulation of the 5CB within the PEM capsules is believed to have occurred as follows. Small molecules such as 5CB (miscible with ethanol) readily diffuse through the semipermeable PEM layers. Upon contact with water, the outer surfaces of the capsules are preferentially wet by water (when terminated with PAH), thus dispersing the 5CB-filled capsules in water. Removal of 5CB from outside the capsules upon addition of water is less effective when the outermost layer of the capsule wall is PSS, rather than PAH.

Bright field micrographs of the 5CB-(PSS/PAH)$_3$/PSS capsules show LC droplets with smaller LC droplets attached to the outer surfaces (data not shown). When the capsule wall is terminated with PSS, 5CB adheres to the capsule wall, likely due to the favorable interaction between PSS and 5CB. This is consistent with the inventors earlier observations, where stable 5CB emulsions were formed in the presence of PSS but not with PAH.

The 5CB-filled capsules are dispersions that are kinetically stable over a wide range of conditions. To illustrate this kinetic stability, one may consider the work required to remove the 5CB from the core of the capsule. This work can be written as:

$$\gamma_{5CB\text{-}W} + \gamma_{PSS\text{-}W} - \gamma_{PSS\text{-}5CB},$$

where $\gamma_{5CB\text{-}W}$, $\gamma_{PSS\text{-}W}$ and $\gamma_{PSS\text{-}5CB}$ are the interfacial energies of the 5CB-water, water-PSS-terminated, and 5CB-PSS-terminated interfaces, respectively.

By defining a contact angle of a droplet of 5CB on a PSS-terminated PEM under water as $\cos\theta = (\gamma_{PSS\text{-}W} - \gamma_{PSS\text{-}5CB})/\gamma_{5CB\text{-}W}$, the work of removal of the 5 CB is calculated to be positive (i.e., dispersion is kinetically stable) provided $\cos\theta$ is greater than one. This condition holds true for all contact angles except $\theta = \pi$ and is satisfied for the 5CB and oils reported herein.

Figure 4:
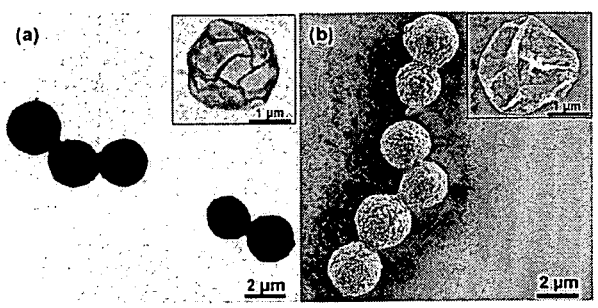
FIG. 4. (a) TEM image of 5CB-filled (PSS/PAH)$_4$ capsules made from MS templates (inset is a TEM image of empty (PSS/PAH)$_4$ capsules). (b) SEM image of 5CB-filled (PSS/PAH)$_4$ capsules made from MS templates (inset is SEM image of empty (PSS/PAH)$_4$ capsules).

The morphology and structural integrity of the 5CB-loaded (PSS/PAH)$_4$ capsules were characterized with transmission electron microscopy (TEM) (FIG. 4a) and scanning electron microscopy (SEM) (FIG. 4b). In contrast to the empty (PSS/PAH)$_4$ capsules (insets in FIGS. 4a and 4b), which collapse upon drying, the 5CB-loaded (PSS/PAH)$_4$ capsules retain a largely spherical shape (FIG. 4). Images of 5CB-loaded capsules obtained using TEM show marked increases in electron density (FIG. 4a), which is attributed to the presence of 5CB in the capsules. SEM demonstrates that the 5CB-loaded (PSS/PAH)$_4$ capsules retain a 3-dimensional structure (FIG. 4b), further confirming 5CB loading.

To determine the amount of 5CB loaded into the (PSS/PAH)$_4$ capsules, the inventors examined the capsules using flow cytometry and UV-visible spectrophotometry. The number of 5CB-loaded (PSS/PAH)$_4$ capsules (made from MS, size 4.7±0.5 μm) in water was determined by flow cytometry to be approximately $9.6 \times 10^4$ particles $\mu L^{-1}$. The 5CB-loaded $(PSS/PAH)_4$ capsule dispersion was then exposed to ethanol to dissolve the LC, and the LC absorbance in the supernatant was measured. By using a UV-visible absorbance calibration curve, the inventors deduced that 88±2% (vol %) of the capsule interior was filled with 5CB. Analysis of the capsules by optical microscopy showed that the capsules were homogeneously filled, with greater than 98% of the capsule population loaded with 5CB.

This general method can also be used to prepare naked LCs emulsions by using $(PMA/PVPON)_4$ capsules as templates. The $(PMA/PVPON)_4$ capsules exploit hydrogen bonding between the PMA and PVPON to facilitate capsule formation.[25] FIG. 4a shows both bright field and fluorescence micrographs of 5CB-loaded $(PMA/PVPON)_4$ capsules prepared from MS in acetate buffer of pH 4 (PMA and PVPON were fluorescently labeled with FITC and AlexaFluor 488, respectively). The uniform fluorescence around the capsule demonstrates that the capsule wall is well-defined (inset in FIG. 5a). Both of the images are similar to the 5CB-loaded $(PSS/PAH)_4$ capsules.

Figure 5:
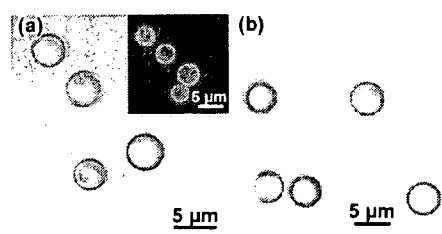
FIG. 5. (a) Bright field micrograph of 5CB-(PMA/PVPON)$_4$ capsules made from MS templates (inset is a fluorescence image of 5CB-filled (PMA-FITC/PVPON-FL488)$_4$ capsules made from MS templates). (b) Bright field optical micrograph of naked 5CB droplets obtained after disassembly of PMA/PVPON layers.

Naked LC emulsions were prepared by disassembling the PMA/PVPON layers at pH 7.5 (FIG. 5b). The absence of fluorescence around the LC droplets suggests that the polymers were completely disassembled and the LC droplets were free from PMA-FITC and PVPON-FL488. Moreover, the size of the droplets did not change after disassembly of the PEM layers, which, as for the PAA/PAH capsules, indicates a high LC loading of the capsules.

The naked LC emulsions are stable over at least seven days after disassembly of PEM layers, which is probably due to the spontaneous adsorption of hydroxyl ions at the oil-water interface. Moreover, the LC droplets can also be readily stabilized by surfactants and lipids after disassembly of the PEM layers (see below).

Figure 6:
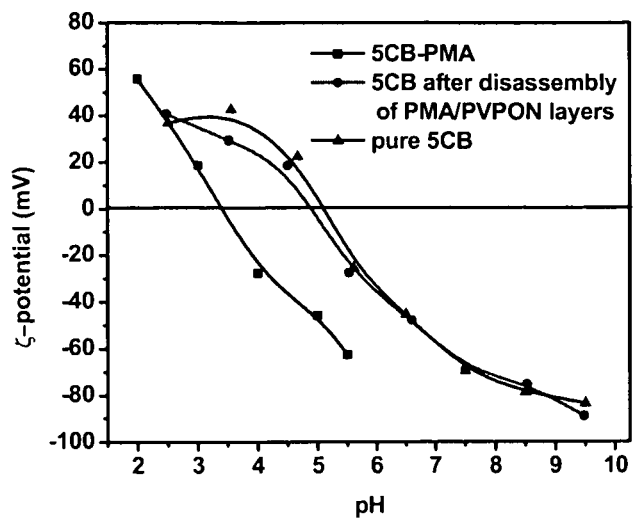
FIG. 6. ζ-potential vs pH for the 5CB-PMA, 5CB after disassembly of PMA/PVPON layers, and pure 5CB emulsions.

Microelectrophoresis experiments showed similar 4-potential vs. pH curves for these emulsions and uncoated 5CB emulsions in water prepared by sonication, with both emulsions having an isoelectric point (IEP)=5.1 (see FIG. 6). In contrast, the ζ-potential measurements of 5CB emulsions coated with $(PMA/PVPON)_4$ have an IEP=3.2. This further suggests that the 5CB droplets are free from PEM layers after the disassembly. Polarized light micrographs of both the $(PMA/PVPON)_4$-coated and naked LC droplets showed that they have similar bipolar configurations (data not shown).

The PAH/PSS capsules were filled to approximately 88 vol % of maximum capacity, and stable emulsions were formed when PSS was the outermost layer. The LCs within the 5CB-loaded $(PSS/PAH)_4$ capsules assumed a boojum/bipolar configuration. Finally, naked LC emulsions were prepared by using degradable $(PMA/PVPON)_4$ capsules as a template.

As can be appreciated from considering the present disclosure, a general and facile method to prepare multilayer-coated and naked oil emulsion droplets is disclosed. The formation of multilayer-coated 5CB, silicone, and paraffin oil droplets highlights that the technique is robust and easily generalizable.

The present methods offer several advantages over microfluidic-based approaches. These include: (i) the ability to readily prepare monodisperse droplets of over a wide range of sizes, as capsule templates can be prepared with diameters as small as approximately 10 nm and as large as millimeters; (ii) the preparation of large quantities of emulsion droplets, as the templating method is parallel and scalable (a typical synthesis using 10 mg of silica template particles results in approximately $10^7$ oil-filled capsules); and (iii) the preparation of emulsion droplets of different composition with well-defined surface functionality. As can be appreciated, this method is robust and can be applied to routinely produce large quantities of oil droplets, including naked monodisperse oil emulsion droplets ranging from predetermined-nanometers to micrometers, or oil emulsion droplets functionalized with a variety of multilayer coatings that can be tailored for specific applications.

Accordingly, the present invention further encompasses the oil emulsion droplets and multilayer-coated oil emulsion droplets prepared by the methods described and claimed herein. In one aspect, the invention provides an oil emulsion comprising monodisperse oil emulsion droplets having a uniform predetermined diameter from about 10 nm to about 10 mm. Such monodisperse oil emulsion droplets preferably have a granulomeric distribution of about 30% or less. In one alternative embodiment, the monodisperse oil emulsion droplets are less than 100% filled with oil.

In certain preferred embodiments, the monodisperse oil emulsion droplets are monodisperse liquid crystal emulsion droplets, preferably having a uniform predetermined diameter of from about 0.1 μm to about 10 μm, and yet more preferably having a granulomeric density of about 30% or less. In certain embodiments, the monodisperse liquid crystal emulsion droplets further comprise an enzymatic substrate or, alternatively, an amphiphile. In other embodiment, the monodisperse liquid crystal emulsion droplets have a single macromolecular assembly species coated on the surface of the droplet.

In Example 6 below, the inventors report a non-limiting example of a general and versatile sensing method based on monodisperse liquid crystal (LC) emulsion droplets to detect and distinguish between different types of bacteria (Gram +ve and −ve) and viruses (enveloped and non-enveloped). An ordering transition in the 4-cyano-4-pentylbiphenyl LC, from a bipolar or nearly bipolar (and not radial) to a radial configuration, is observed when Gram −ve bacteria (*E. coli*) and viruses encapsulated by a lipid envelope (A/NWS/Tokyo/67) are contacted with the micrometer-sized LC droplets. This ordering transition is consistent with the transfer of lipid from *E. coli* and A/NWS/Tokyo/67 onto the interface of the LC droplets. In contrast, the LC droplets do not assume a radial configuration in the presence of Gram +ve bacteria (*Bacillus subtilis* and *Micrococcus luteus*) and non-enveloped viruses (M13 helper phage). The LC droplets can detect a single *E. coli* bacterium, and a small number and a low concentration (104 pfu mL-1) of the A/NWS/Tokyo/67 virus. Monodisperse LC emulsions incubated with phospholipid liposomes (chosen to model the *E. coli* cell wall lipid) reveal that an orientational change from a bipolar to a radial configuration is triggered at an area per lipid molecule of ~46 Å2 ($\sim 1.6 \times 10^8$ lipid molecules per droplet) on a LC droplet. The reported approach represents a novel means to sense and differentiate different types of bacteria and viruses based on their wall/envelope structure, paving the way for the development of a new class of LC microdroplet-based biological sensors.

The significance of the work described below in Example 7, in part, is that size-dependent ordering has been characterized without the need to change parameters of the system such as temperature, interfacial chemistry or the LC. The experimental method also provides scalable quantities of monodisperse LC-filled polymeric shells that are sufficient to be technologically useful. The size and interfacial chemistry of these LC-filled shells can be controlled at a level that has not previously been possible, and thus they open up a range of technological opportunities where size-dependent ordering of LCs can be exploited. For instance, the interaction of light with LCs is influenced by the ordering of the LC; control of the size of LC droplets provides a general approach to manipulate this interaction. In addition, a particularly promising set of opportunities revolve around the design of LC materials that respond to chemical and biological molecules, as the response of the LCs can be tuned via subtle changes in size and interfacial conditions (e.g., binding events).

Based upon the monodisperse droplets manufactured by the methods described and claimed herein, the invention further provides a liquid crystal-based method for detecting a target analyte in a sample. Such a method includes steps of: (a) contacting a sample with a monodisperse liquid crystal droplet; and (b) detecting a change of orientation of liquid crystal contained within the monodisperse liquid crystal droplet wherein the change of orientation corresponds to the presence of a target analyte contained within the sample.

In certain embodiments, the target analytes detected in the method are bacteria, or alternatively, a virus. The monodisperse liquid crystal droplet used in the method preferably has a predetermined diameter from about 0.1 µm to about 10 µm and, furthermore, a plurality of droplets utilized in the method, as is the preferred technique, preferably have a granulomeric distribution of about 30% or less.

In yet another aspect, the invention provides a liquid crystal-based method of detecting an enzymatic activity. Such a method includes steps of: (a) contacting an enzyme with a monodisperse liquid crystal droplet decorated with a substrate of the enzyme; and (b) detecting a change of orientation of liquid crystal contained within the monodisperse liquid crystal droplet wherein the change of orientation corresponds to the enzyme exhibiting enzymatic activity toward the substrate. Example 11 below describes one particular embodiment of such a method.

The invention also encompasses LC-based sensors using microdroplets manufactured according to the present methods. Therefore, the invention further provides a liquid crystal-based sensor for detecting a target analyte in a sample. Such a sensor includes: (a) an emulsion including monodisperse liquid crystal droplets; and (b) a detector capable of detecting and reporting a change in orientation of liquid crystal contained in the monodisperse liquid crystal droplets in response to the monodisperse liquid crystal droplets contacting a target analyte contained in a sample. The construction and use of an exemplary biosensor according to the invention is detailed in Example 6 below.

The monodisperse liquid crystal droplets utilized in the sensor preferably have a uniform predetermined diameter from about 0.1 µm to about 10 µm and, yet more preferably, have a granulomeric distribution of about 30% or less.

The following examples describing materials and methodology are offered for illustrative purposes only, and are not intended to limit the scope of the present invention.

IV. EXAMPLES

Example 1

Materials, Methods and Instrumentation

Materials. Poly(sodium-4-styrenesulfonate) (PSS, $M_w$ 70 kDa), poly (allylamine hydrochloride) (PAH, $M_w$ 70 kDa), poly(methacrylic acid) (PMA, $M_w$ 15 kDa), poly(vinylpyrrolidone) (PVPON, $M_w$ 12 kDa), fluorescein isothiocyanate, (FITC), hydrofluoric acid, 3-aminopropyltriethoxysilane (APTS), silicone oil, paraffin oil, sodium acetate, sodium hydrogen phosphate, acetic acid, and sodium chloride (NaCl) were purchased from Sigma-Aldrich, and used as received. The nematic LC 4-cyano-4'-pentylbipenyl (5CB) was purchased from Merck (Germany). Mesoporous (MS) and nonporous silica were purchased from Tessek (Czech Republic) and Microparticles (Germany), respectively. APTS-modified MS particles were prepared as described previously. FITC-labeled PAH (FITC-PAH) and PMA-FITC was synthesized as described elsewhere.

Methods. Fluorescent labelling of PVPON was performed in a 10 g $L^{-1}$ solution of PVPON in pH 7.5 tris(hydroxymethyl)aminomethane/ethylenediamine tetraacetic acid (TRIS/EDTA) buffer in the presence of 1 mM tris(2-carboxyethyl)phosphine hydrochloride (TCEP) and 0.1 g $L^{-1}$ of Alexa Fluor 488 maleimide. The reaction was allowed to proceed overnight, after which the polymer was purified on a NAP-5 column and recovered by freeze drying. An inline RIOs/Origin system was used to produce high-purity water.

Instrumentation. The orientation of LC within the emulsion droplets was observed with plane-polarized light in transmission mode on an Olympus IX 71 inverted fluorescence microscope with cross polarizers. Bright field images were taken using the same microscope. In both cases, a 60× objective was used and images were captured with a color camera. Confocal laser scanning microscopy (CLSM) images were taken with a Leica DMIRE2 confocal system. Optical microscopy was performed by placing the sample between two cover slips. Scanning electron microscopy (SEM, FEI Quanta 200 FEG, operated at 2 kV) and transmission electron microscopy (TEM, Philips CM120 BioTWIN, operated at 120 kV) were used to examine the morphology of the particles. A HP 8453 UV-vis spectrophotometer (Agilent, Palo Alto, Calif.) was used to determine the concentration of LC in the capsules. ζ-potentials were measured on a Zetasizer 2000 (Malvern) instrument.

Example 2

Preparation of PSS/PAH Capsules 0.5 mL of polyelectrolyte solution (1 mg $mL^{-1}$ containing 0.5 M NaCl) was added into 5 mg of APTS-MS particles. The mixture was incubated with agitation for 10 min. After adsorption, the mixture was centrifuged (470 g, 1 min) and the supernatant was removed. The pellets were washed thrice with water, and the next polyelectrolyte layer was then adsorbed. The entire process was repeated until the desired number of layers was achieved. In the next step, the particle template was removed by exposure to 1 mL of 5 M HF solution at 20° C. for 2 min, and the mixture was centrifuged at 4500 g for 5 min. The supernatant was removed and the pellet was washed five times with water.

Example 3

Incorporation of Oils into PEM Capsules

PEM capsules dispersed in water were centrifuged and the supernatant removed. The pellet was redispersed in 0.5 mL of ethanol and centrifuged at 4500 g for 5 min. This procedure was repeated. The resulting pellet of ethanol-filled PEM capsules was then contacted with 0.1 mL of 5CB and the mixture was incubated for 24 hrs at 22° C. The 5CB-filled PSS/PAH (LC-PSS/PAH) capsules were centrifuged (approximately 1000 g) for 1 min and washed three times with water to remove excess 5CB from the capsule walls. The empty PSS/PAH capsules were dispersed in acetone and toluene for the infiltration of silicone oil and paraffin oil, respectively. 0.5 mL of silicone or paraffin oil was added to the PEM capsule dispersion and the same procedure outlined for 5CB was followed. Experiments to determine the amount of 5CB loaded into the (PSS/PAH)$_4$ capsules were repeated in triplicate.

Example 4

Preparation of Naked LC Emulsions

PMA and PVPON solutions (0.5 mg mL$^1$ in acetate buffer, pH 4) were used for the preparation of PMA/PVPON capsules. All washing steps in the preparation of the PMA/PVPON capsules were performed with acetate buffer (pH 4). The 5CB filling was performed as described for the PSS/PAH capsules. Disassembly of the PMA and PVPON layers was accomplished by exposing the 5CB-filled capsules to a pH 7.5 solution for 20 min to break the hydrogen bonding between the PMA and PVPON, followed by centrifugation at 4500 g for 5 min and washing in 0.5 mL of phosphate buffer at pH 7.5.

Example 5

Non-Spherical Templates Based on Assemblies of Particles

Figure 7:
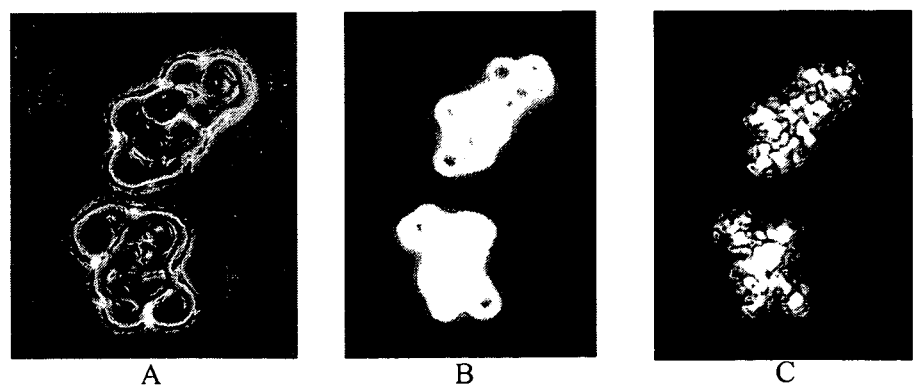
FIG. 7. Micrographs illustrating filling of LC in a non-spherical template formed due to particle aggregation during multilayer coating process. (A) Bright field micrograph. (b) Fluorescent micrograph. (c) polarized micrograph.

In this example, a non-spherical template for the multilayer coating process was prepared by assembly of silica particles (with diameters of 1 µm). After multilayer coating using PAH and PSS (as described in examples above), the non-spherical templates formed from silica particles were etched with HF (as described in example 2) to obtain capsules which were non-spherical in shape. These capsules were filled with 5CB following the procedure described in example 3 to obtain 5CB droplets confined in a non-spherical geometry. FIG. 7 shows (a) a bright field micrograph, (b) fluorescent micrograph (obtained using fluorescently labeled PEs) and (c) a polarized micrograph which demonstrate that a non-spherical capsule formed from PEs surrounds a non-spherical droplet of liquid crystal. This result demonstrates that non-spherical templates can be used to form non-spherical capsules that contain oil. It also demonstrates that assemblies of particles can be used as templates in the methods and materials of this invention.

Example 6

Figure 8:
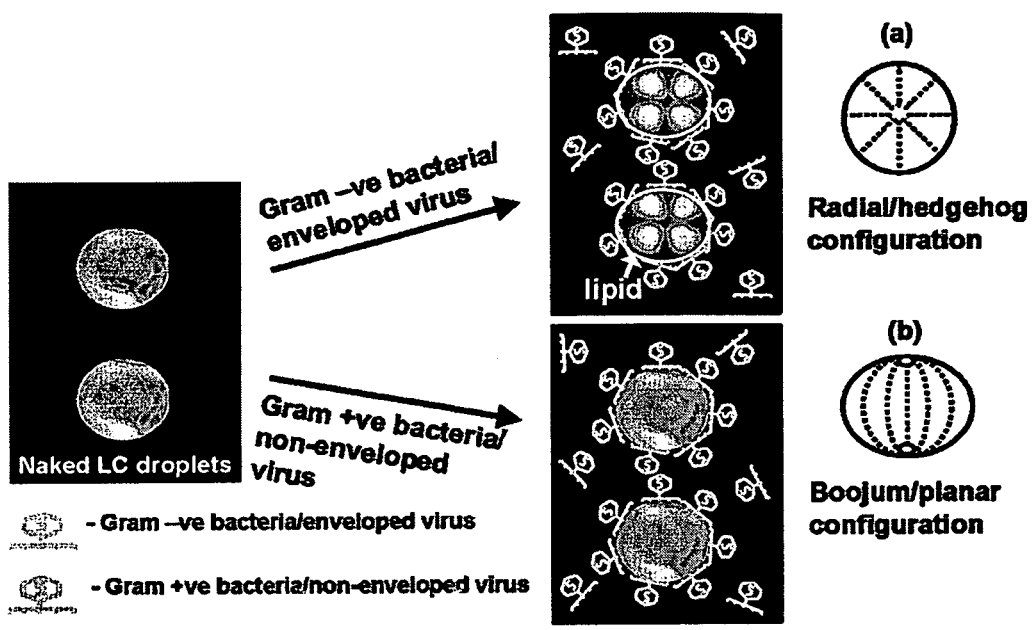
FIG. 8. Schematic representation of the interaction of viruses or bacteria with naked LC emulsions. Cartoons (a) and (b) depict the radial and boojum orientation of LCs, respectively. The LC droplets shown are polarized light micrographs of 5CB droplets.

Monodisperse Liquid Crystal Emulsions as Biological Sensors for the Optical Detection of Bacteria and Viruses Herein, the inventors report a new and versatile method employing monodisperse LC emulsion droplets that detects and distinguishes between different structural classes of biological species (bacteriaGram +ve and –ve; virusesenveloped and non-enveloped) with high sensitivity based on their cell-wall/envelope structure (FIG. 8). The inventors investigate the ordering of LCs within monodisperse nematic LC droplets (4-cyano-4-pentylbiphenyl, 5CB) in contact with different types of viral/bacterial particles. The inventors focus on characterization of the LC response (ordering transition) to the lipid components of bacteria and viruses. Three different bacteria (*Escherichia coli* (*E. coli*, Gram –ve), *Bacillus subtilis* (*B. subtilis*, Gram +ve), and *Micrococcus luteus* (*M. luteus*, Gram +ve) and two different viruses (M13 helper phage (non-enveloped) and A/NWS/Tokyo/67 (enveloped)) were chosen for our study. *E. coli* and *B. subtilis* are rod-shaped, *M. luteus* is spherical, M13 helper phage is an icosahedron, and A/NWS/Tokyo/67 is bullet-shaped. These bacteria and viruses possess distinct structural differences (Table 1).

TABLE 1

Properties of Gram +ve and –ve Bacteria

| Structural Feature | Gram +ve bacteria B. subtilis and M. luteus | Gram –ve bacteria E. coli |
|---|---|---|
| Thickness of wall | Thick (20-80 nm) | Thin (10 nm) |
| Number of layers | 2 | 1 |
| Peptidoglycan (murein) content (wt %) | >50 | 10-20 |
| Teichoic acids in wall | Present | Absent |
| Lipid and lipoprotein content (wt %) | 0-3 | 58 |
| Protein content (wt %) | <2 | 9 |
| Lipopolysaccharide content (wt %) | 0 | 13 |

The inventors demonstrate that LC emulsions can be used to sense the Gram –ve bacteria *E. coli* and the enveloped virus A/NWS/Tokyo/67 in water. By using a model system comprised of a purified phopholipid (to represent a key component of *E. coli* cell wall), they also quantify the minimum number of lipid molecules needed to induce an orientational change in the LC droplets. Although the ordering of LC thin films can be used to report viruses captured on solid surfaces, dispersed phases of LCs (emulsion droplets) offer a variety of potential advantages in terms of sensitivity, quantification, speed and ease of handling. Furthermore, the droplet-based method can be used to screen a large number of bacterial/virus samples and allows for the detection of specific bacteria/viruses by decorating the surface of the LC droplets with antibodies to concentrate and localize particular bacteria/viruses from dilute solutions at the surfaces of the LC droplets.

Results and discussion. Silica particles with 8 nm pores (5±0.5 µm) were first amine-functionalized by grafting 3-aminopropyltriethoxysilane (APTS) to the particle surface (see Methods). The APTS-functionalized silica particles were next coated with polyelectrolytes (PEs), and the coated particles were exposed to hydrofluoric acid (HF) to etch the silica core, resulting in the formation of hollow polyelectrolyte multilayer (PEM) capsules. Poly(methacrylic acid) (PMA)/poly(N-vinylpyrrolidone) (PVPON) multilayers were chosen because the PMA/PVPON layers can be readily disassembled due to disruption of the hydrogen bonding between the layers by changing the pH of the solution. APTS-functionalized silica is positively charged; hence, the anionic PMA was deposited as the first layer, followed by the alternate deposition of PVPON and PMA to deposit a total of eight layers. To permit imaging by fluorescence microscopy, PMA was labeled with fluorescein isothiocyanate (FITC). After etching the silica cores with HF, the capsules were washed five times with acetate buffer (pH ~4) and twice with ethanol. 5CB was then infiltrated through the semipermeable walls of the PEM capsules, and excess 5CB was removed from outside the PEM capsules by contacting the capsules with water. This procedure resulted in the formation of monodisperse PEM-coated LC droplets (denoted as 5CB-(PMA/PVPON)$_4$). Naked LC emulsion droplets were prepared by disassembling the PMA/PVPON layers on the LC emulsions upon exposure to pH 7.5 solutions. The absence of fluorescence around the LC droplets suggests that the polymers were completely disassembled and that the LC droplets were free from the PEs.

Sizing of the naked LC emulsion droplets from microscopy images yielded diameters of 4.7±0.5 m. The naked LC droplets were incubated with bacteria/viruses (purified by centrifugation to remove all cell debris) in PBS buffer of pH ~7.2 for 30 min in a humid environment on a glass slide. After incubation, the bacteria/virus-decorated LC droplets were examined by optical microscopy. 5CB-loaded poly(sodium-4-styrenesulfonate) (PSS)/poly(allylamine hydrochloride) (PAH) capsules were prepared as described previously.

FIG. 9a shows a bright field optical micrograph of naked 5CB droplets in contact with E. coli (Gram −ve bacteria, ~5×10$^5$ cells mL-1). Inspection of FIG. 9a shows naked LC droplets surrounded by E. coli. Polarized light microscopy was used to study the orientation of the 5CB within the droplets. Past studies have demonstrated that the orientation of LCs within a droplet depends on several factors, such as the elasticity of the LC, the orientation of the LC easy axis at the interface of the droplet, and the anchoring energy of the LC. A polarized light micrograph (crossed polars) of naked 5CB droplets surrounded by E. coli (FIG. 9b) shows a symmetric cross pattern (and a point defect is evident at the center of the LC droplet in the bright field micrograph in FIG. 9a), thus indicating that the 5CB droplets have assumed a radial configuration. In contrast, naked LC droplets in PBS buffer (in the absence of E. coli) show a bipolar configuration (FIG. 9c), which is caused by planar anchoring of the LC at the droplet interface and two point defects at the poles of the droplet. To confirm that the change in the orientation of the naked LC droplets is due to the presence of the E. coli and not, for example, due to the presence of the medium/buffering salt (used in the cell growth procedure) in the solution, the inventors incubated the naked LC droplets with a supernatant solution obtained by centrifugation (600 g, 1 min) of the E. coli (~5×10$^5$ cells mL-1). This experiment did not result in LC droplets with a radial configuration and/or cause any measurable change in the orientation of the LC droplets relative to that observed in water, demonstrating that the change in the orientation of the LC evident in FIG. 9b is due to the presence of E. coli.

Figure 10:
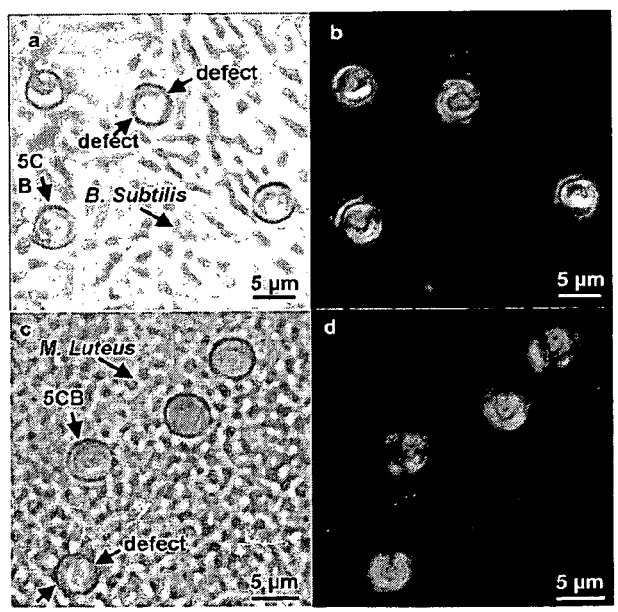
FIG. 10. (a) Bright field micrograph of naked 5CB droplets with B. subtilis and (b) corresponding polarized light micrograph (crossed polars). (c) Bright field micrograph of naked LC droplets with M. luteus and (d) corresponding polarized light micrographs (crossed polars).

Next, the inventors investigated the orientational behavior of naked LC droplets with Gram +ve bacteria. B. subtilis (~6×10$^5$ cells mL$^{-1}$) was chosen for the current study because it has similar physical dimensions as E. coli and yet exhibits distinct structural differences (Table 1). FIG. 10a shows the bright field micrograph of naked LC droplets surrounded by B. subtilis. A polarized light micrograph (crossed polars) of naked 5CB droplets surrounded by B. subtilis (FIG. 10b), reveals that the 5CB droplets have a bipolar or nearly bipolar configuration (and not radial configuration), showing no substantial change in the LC droplet orientation upon incubation with B. subtilis. This is further confirmed by contacting another Gram +ve bacteria, M. luteus, (~5×10$^5$ cells mL$^{-1}$) with naked LC droplets, which also does not cause a change in the orientation of the LC droplets to a radial configuration (FIGS. 10c and 10d). We note that similar concentrations of E. coli, B. subtilis, and M. luteus were used in these studies. These observations confirm that monodisperse, naked LC droplets can be used to sense Gram −ve bacteria and distinguish between Gram +ve and −ve bacteria.

Figure 11:
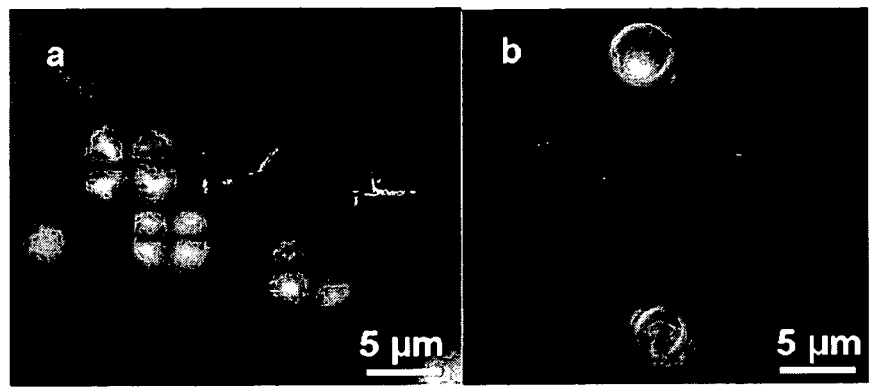
FIG. 11. Polarized light micrographs (crossed polars) of (a) naked 5CB droplets with A/NWS/Tokyo/67 and (b) naked 5CB droplets with M13 helper phage.

FIG. 11 shows the polarized light micrograph (crossed polars) of naked 5CB droplets surrounded by A/NWS/Tokyo/67 (10$^6$ pfu mL$^{-1}$, encapsulated viruses, FIG. 11a) and M13 helper phage (10$^6$ pfu mL$^1$, non-encapsulated viruses, FIG. 11b), showing that the 5CB droplets have assumed radial and bipolar or nearly bipolar configurations (the latter configurations being not radial), respectively. The control experiment where the LC droplets were incubated with the supernatant solution obtained by centrifuging A/NWS/Tokyo/67 viruses under similar conditions (see Methods) did not show a radial configuration and/or cause any measurable difference in the orientation of LC droplets. This indicates that lipid molecules, if shed by the virus, are not sufficient to trigger the transition in these experiments and that the change in LC orientation occurs only upon contact of the A/NWS/Tokyo/67 virus with the LC droplets, which results in lipid transfer from the virus to the LC droplets. These results demonstrate that naked LC droplets can be used to sense enveloped viruses and distinguish enveloped from non-enveloped viruses.

Figure 12:
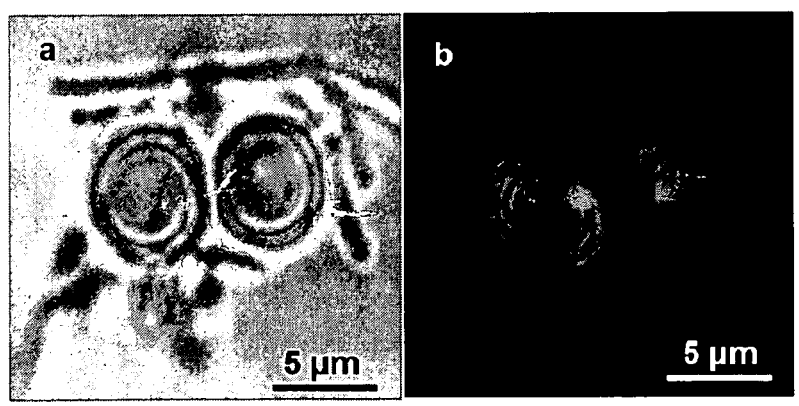
FIG. 12. (a) Bright field micrograph of 5CB-(PSS/PAH)$_4$ droplets with E. coli and (b) corresponding polarized light micrographs (crossed polars).

The results above support the hypothesis that the radial configuration of naked LC droplets observed with E. coli and A/NWS/Tokyo/67 viruses is due to the presence of lipid within the outer wall/coat of each species. This radial configuration contrasts with that of the non-radial configuration observed with Gram +ve and non-encapsulated viruses. The inventors previous studies have shown that lipid-laden interfaces cause LCs such as 5CB to assume a homeotropic orientation (and thus radial alignment in a droplet). Control experiments revealed that neither the cell debris remaining in the virus sample nor the media/buffering salt cause the radial alignment of naked LC droplets. It may be possible that the packing (spatial organization) of bacteria around the droplet of bacteria/viruses may also influence the ordering of naked LC droplets. The inventors also note that E. coli and B. subtilis have a similar shape and size, yet they give rise to a different orientation of the LC droplets. On the other hand, B. subtilis and M. luteus have different shapes and sizes, yet they give rise to the same orientation. This observation leads to the conclusion that it is unlikely that the size, shape, and packing of the bacteria/viruses determine the orientation of LC droplets. Interestingly, the inventors observe that incubation of PEM-coated LC droplets ((PSS/PAH)$_4$-5CB)) with E. coli results in a bipolar configuration of the LC droplets, which suggests that naked LC droplets are required to trigger the change in the orientation (FIG. 12) because the PSS/PAH layers prevent transfer of the lipid from bacteria/viruses to the LC droplets. The inventors also note that the PSS/PAH layers are highly stable in different conditions, including a wide range of pH (2-10) and salt concentrations (0-1 M).

Several additional observations provide further support for the proposition that the cell wall/envelope of the bacteria/viruses leads to the radial configuration of naked LC-droplets. The inventors postulate that the change in the orientation of naked 5CB droplets occurs as follows. During the incubation, E. coli/A/NWS/Tokyo/67 surrounds the naked LC droplets and the lipid from the E. coli (cell wall) or A/NWS/Tokyo/67 (envelope) transfers to the interface of the naked LC droplets, inducing the change in orientation of the LC within the droplets. This is further confirmed by contacting fluorescently labeled liposomes (made from 1,2,dimytristoyl-sn-glycero-3-phosphoethanolamine-N-(7-nitro-2-1,3-benzoxo diazo-4-yl-ammonium salt) with the naked LC droplets. The inventors note that phosphoethanolamine lipid is the major (54%) component of lipid present in E. coli cell walls, and thus the liposome can be viewed as a simple model of a bacterial cell wall. After a 20 min incubation of the fluorescently labeled liposomes (diameter of ~0.7 μm) with the naked LC droplets, the orientation of LC droplets surrounded by liposomes changed from bipolar to radial (top three droplets in FIG. 13c). A fluorescence micrograph of the same droplets (FIG. 13b) also shows bright fluorescence over the naked LC droplet, confirming transfer of lipid from the liposomes to naked LC droplets. On the other hand, the LC droplet in FIG. 13c that does not exhibit radial ordering of the LC (lower left corner of image) is associated with lower levels of lipid (and fluorescence), as seen in FIG. 13b.

Figure 14:
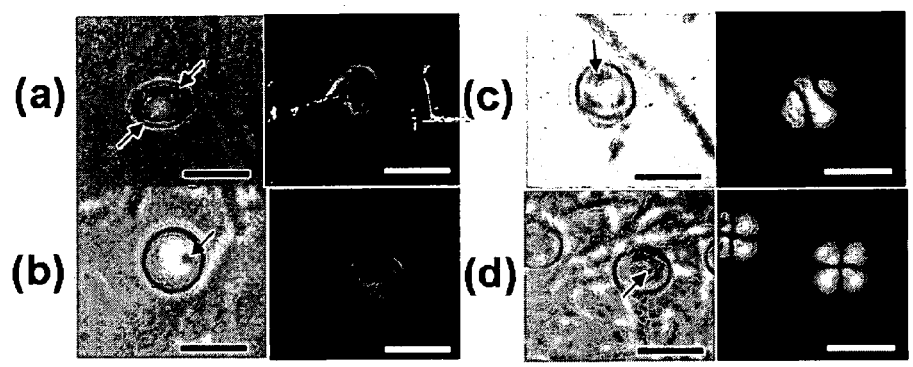
FIG. 14. Bright field and polarized micrograph of naked LC droplets in the (a) absence and (b-d) presence of E. coli. Different droplets are shown in (a)-(d). The scale bars are 5 μm.

The orientation of the LC droplets also depends on the number of bacteria encountered by the LC droplets. FIG. 14 shows bright-field and polarized light micrographs of naked LC droplets. In the absence of any E. coli on the surface of the naked LC droplets, the inventors observed a bipolar LC configuration (FIG. 14a). The presence of a small number of E. coli leads to ordering transitions in the LC droplets. Distinguishable LC droplet states (FIG. 14b-d) are observed when a small number of bacteria (1-5) are near/in contact with the droplets. The inventors postulate that the difference in the orientation of naked 5CB droplets with the number of bacteria on the surface of LC droplets results from the different concentration of lipid on the LC droplet surface, as transferred from E. coli This is consistent with recent observations of continuous LC ordering transitions within droplets from bipolar to radial ordering, via disclination loops, escaped-radial and preradial topological defects, with increasing surfactant concentration. These observations demonstrate that a single Gram –ve bacterium and a small number of enveloped-viruses can be detected by using naked LC droplets.

Figure 15:
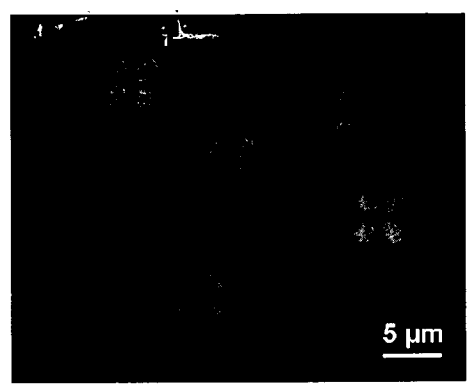
FIG. 15. Polarized light micrographs (crossed polars) of naked 5CB droplets with A/NWS/Tokyo/67 ($10^4$ pfu mL$^{-1}$).

This is further confirmed by incubation of naked LC droplets with different concentrations of the A/NWS/Tokyo/67 virus ($10^6$, $10^5$, and $10^4$ pfu mL$^{-1}$) in solution Inspection of polarized light micrographs suggests that an ordering transition to radial ordering in the LC droplets is observed even at $10^4$ pfU mL$^{-1}$ (FIG. 15). Moreover, the detection limit of viruses can be decreased by decorating the surface of the naked LC droplets with specific antibodies so as to concentrate and localize viruses from dilute solutions at the surfaces of the LC droplets. Specific viruses can also be detected in bacteria/virus mixtures using such an approach.

Figure 9:
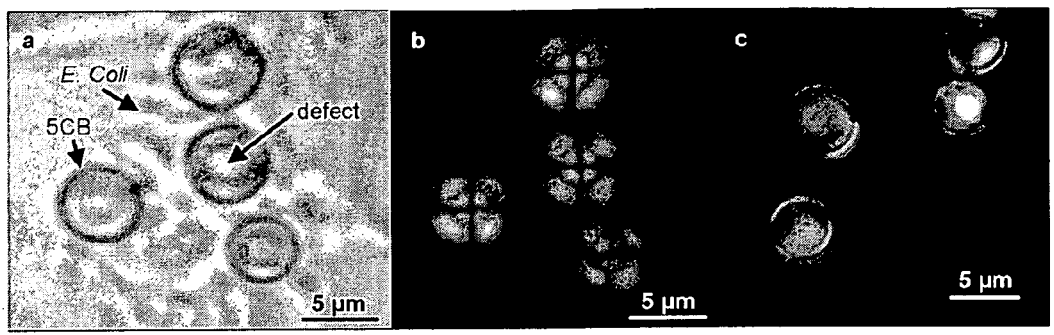
FIG. 9. (a) Bright field micrograph of naked 5CB droplets with E. coli, (b) corresponding polarized light micrographs (crossed polars), and (c) polarized light micrograph of naked 5CB droplets obtained after disassembly of PMA/PVPON layers in phosphate buffer of pH 7.2.

The design of biosensors based on LC droplets will be enabled by a quantitative understanding of the amount of lipid in biological species that is required to trigger an ordering transition in a LC droplet. Moreover, monodisperse droplet systems permit the reliable and precise quantification of lipid molecules adsorbed on LC droplets. The inventors determined the minimum number of lipid molecules required to induce the ordering transition in a naked LC droplet from a bipolar to a radial configuration, as described below. The monodisperse nature of the LC droplets allowed the total LC-aqueous interfacial area to be accurately determined. Approximately $10^5$ naked LC droplets (determined by flow cytometry) were incubated with 100 μL of a fluorescently labeled lipid (1,2, Dimytristoyl-sn-Glycero-3-phosphoethanolamine-N-(7-nitro-2-1,3-benzoxo diazo-4-yl-ammonium salt) solution at different concentrations for 2 h. Following incubation, the naked LC droplets were centrifuged and washed three times with water to remove the excess lipid. Subsequently, the LC droplets were dissolved in ethanol (200 μL) and the fluorescence intensity of the lipid was measured. By using a fluorescence intensity calibration curve, the inventors deduced the number of lipid molecules present on the surface of naked 5CB droplets. The area per lipid molecule required to induce the ordering transition of a naked LC droplet from planar to radial is determined to be ~46 Å$^2$ ($1.6 \times 10^8$ lipid molecules per ~5 μm LC droplet; [lipid] ~2.5 μM). The inventors found that upon further increasing the lipid concentration, from 2.5 to 20 μM, the LC orientation remained unchanged. The number of lipid molecules present in a single E. coli cell is reported to be ~$1.5 \times 10^7$. This suggests that approximately 10 bacteria (containing $1.5 \times 10^8$ lipid molecules) are needed to saturate the surface of the LC droplet with lipid (and thus change the orientation of a LC droplet from boojum to radial), which is consistent with the inventors study of the influence of the E. coli number on LC droplet ordering (FIGS. 9 and 14).

In conclusion, the inventors have demonstrated that LC emulsions can be used to detect Gram –ve bacteria/encapsulated viruses and distinguish between different types of bacteria (Gram +ve and –ve) and viruses (encapsulated and non-encapsulated). They found that Gram –ve bacteria and encapsulated viruses with a lipid envelope, when brought into physical contact with LC droplets, cause radial ordering of LC droplets due to the transfer of lipid from their surfaces to that of the LC droplets. The LC emulsions were also shown to detect low concentrations (up to $10^4$ pfu mL$^{-1}$) of virus. The inventors also determined the minimum area per lipid molecule on a naked LC droplet surface (~46 Å$^2$) required to induce a planar to radial ordering transition. This method may be used to screen very large numbers of samples, and sets the framework for the development of a rapid and sensitive screening assay for bacteria and viruses based on their structural features.

Materials. Poly(sodium-4-styrenesulfonate) (PSS, $M_w$ 70 kDa), poly (allylamine hydrochloride) (PAH, $M_w$ 70 kDa), poly(methacrylic acid) (PMA, $M_w$ 15 kDa), poly(vinylpyrrollidone) (PVPON, $M_w$ 12 kDa), flourescein isothiocyanate (FITC), hydrofluoric acid, 3-aminopropyltriethoxysilane (APTS), sodium acetate, sodium hydrogen phosphate, acetic acid, formalin, kanamycin and sodium chloride (NaCl) were purchased from Sigma-Aldrich, and used as received. The nematic LC 4-cyano-4'-pentylbipenyl (5CB) was purchased from Merck (Germany). Mesoporous silica (MS) spheres were purchased from Tessek (Czech Republic). APTS-modified MS particles were prepared as described previously. [Wang, Y. J.; Caruso, F. Template synthesis of stimuli-responsive nanoporous polymer-based spheres via sequential assembly. Chem. Mater. 2006, 18, 4089-4100.] FITC-labeled PAH (PAH-FITC) [Caruso, F.; Yang, W. J.; Trau, D.; Renneberg, R. Microencapsulation of uncharged low molecular weight organic materials by polyelectrolyte multilayer self-assembly. Langmuir 2000, 16, 8932-8936.] and PMA (PMA-FITC)[Zelikin, A. N.; Quinn, J. F.; Caruso, F. Disulfide cross-linked polymer capsules: En route to biodeconstructible systems. Biomacromolecules 2006, 7, 27-30.] and Alex Flour 488-labeled PVPON(PVPON-AF488)[Zelikin, A. N.; Such, G. K.; Postma, A.; Caruso, F. Poly(vinylpyrrolidone) for bioconjugation and surface ligand immobilization. Biomacromolecules 2007, 8, 2950-2953.] were synthesized as described elsewhere. An inline RIOs/Origin system was used to produce high-purity water.

Preparation of PSS/PAH and PMA/PVPON Capsules. 0.5 mL of polyelectrolyte solution (0.5 mg mL$^{-1}$ in acetate buffer, pH 4) was added to 5 mg of APTS-MS particles. The mixture was incubated with agitation for 10 min. After adsorption, the mixture was centrifuged (470 g, 1 min) and the supernatant was removed. The pellets were washed three times with acetate buffer (pH 4), and the next polyelectrolyte layer was then adsorbed. The entire process was repeated until the desired number of layers was achieved. In the next step, the particle template was removed by exposure to 1 mL of 5 M HF solution at 20° C. for 2 min, and the mixture was centrifuged at 4500 g for 5 min. The supernatant was removed and the pellet was washed five times with acetate buffer (pH 4). PSS and PAH solutions (1 mg mL$^{-1}$ containing 0.5 M NaCl) were used for the preparation of PSS/PAH capsules. All washing steps in the preparation of the PSS/PAH capsules were performed with water.

Incorporation of 5CB into PEM Capsules. PEM capsules dispersed in water were centrifuged and the supernatant removed. The pellet was redispersed in 0.5 mL of ethanol and centrifuged at 4500 g for 5 min. This procedure was repeated. The resulting pellet of ethanol-filled PEM capsules was then contacted with 0.1 mL of 5CB in a 0.5 mL Eppendorf tube and the mixture was incubated for 24 h at 22° C. The 5CB-filled PMA/PVPON (LC-PMA/PVPON) capsules were centrifuged (~1000 g) for 1 min and washed three times with acetate buffer (pH 4) to remove excess 5CB from the capsule walls. The 5CB-filled PSS/PAH (LC-PSS/PAH) capsules were washed with water to remove excess 5CB from the capsule walls.

Preparation of *E. coli, B. subtilis* and *M. luteus*. *E. coli* Bacteria was streaked out on a 1XYT agar plate and incubated at 37° C. overnight. A single colony was inoculated into 10 mL of 1XYT liquid medium and incubated at 37° C. with shaking (50 g) for approximately 16-18 h. After incubation, the bacteria were centrifuged (400 g, 1 min), the supernatant was removed, and the bacteria were washed twice in 10 mL PBS. The final pellet was resuspended in 3 mL of PBS. The incubation temperature was 23° C. for *Bacillus subtilis* and *M. luteus*, and the above-described procedure was used.

Preparation of A/NWS/Toykyo/67 Viruses. An influenza virus culture A/NWS/Toykyo/67 was grown in the allantoic cavity of embryonated eggs. Allantoic fluid was clarified at 6500 g in a JA14 rotor, and viruses from the supernatant were concentrated by ultracentrifugation in a Beckman Type 19 rotor at 10,000 g for 2 h. The viruses were resuspended in PBS and fixed in 2% formalin (37%) in 0.15 M NaCl. The final virus titer was ~$10^{10}$ pfu mL$^{-1}$.

Preparation of M13 Helper Phage Viruses. A single colony of *E. coli* TG1 (Stratagene) was inoculated into 10 mL 2YT broth and incubated with shaking at 37° C. overnight. This culture was diluted 1:100 into fresh 2YT broth and incubated until $OD_{600\,nm}$. Helper phage was added at a multiplicity of infection 20:1 (i.e., ca. 200 mL culture requires ~$1.6 \times 10^{12}$ pfu mL$^{-1}$ of helper phage). Cultures were incubated at 37° C. without shaking for 30 min. Kanamycin (25 μg mL$^{-1}$) was added and the culture was incubated at 37° C. The culture supernatant (containing helper phage) was collected via centrifugation at 6500 g for 15 min. The supernatant was heated at 65° C. for 15 min. Following this, cellular debris was removed via centrifugation at 12,500 g. The supernatant containing helper phage was filtered through a 0.45 μm filter cartridge.

Incubation of Bacteria/Viruses with 5CB proplets. Disassembly of the PMA and PVPON layers was accomplished by exposing the 5CB-filled capsules to a pH 7.5 solution for 20 min to disrupt the hydrogen bonding between the PMA and PVPON, followed by centrifugation at 2000 g for 2 min and washing in 0.5 mL of phosphate buffer at pH 7.5. A glass slide was washed with ethanol followed by MilliQ water. A given concentration of bacteria/virus solution was added to the naked 5CB droplets on a glass slide and incubated for ~30 min at room temperature. After 30 min, the glass slide was examined under a microscope. The inventors note that all of the above experiments were performed with the purified virus and bacteria samples. The control experiments were conducted by incubating the naked LC droplets with supernatant solution under similar conditions, and by removing the virus/bacteria by centrifugation.

Determination of Number of Lipid Molecules on the LC proplets. To determine the number of lipid molecules present on the naked LC droplets, the inventors examined fluorescently labeled lipid-decorated LC droplets using flow cytometry and fluorescence spectrophotometry. The number of lipid molecules adsorbed on the LC droplets was determined by flow cytometry. The lipid-coated LC droplets were then exposed to ethanol (150 μL) to dissolve the LC and lipid, and the fluorescence from the lipid was measured. By using a fluorescence calibration curve, the number of lipid molecules on the lipid surface was determined.

Figure 13:
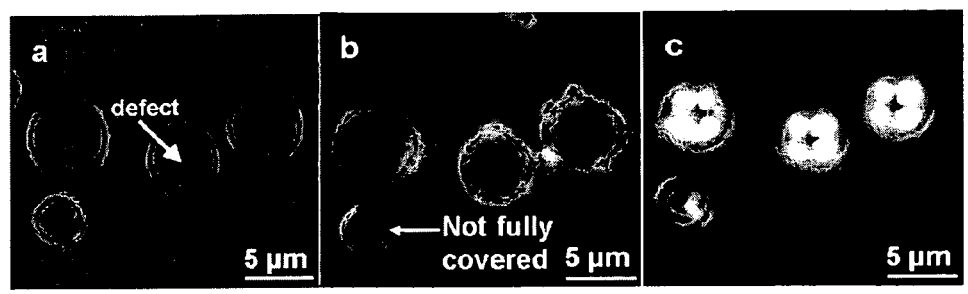
FIG. 13. (a) Bright field micrograph of naked 5CB droplets incubated with fluorescently labeled liposomes, (b) corresponding fluorescence micrograph, and (c) corresponding polarized light micrographs (crossed polars).

Instrumentation. The orientation of LC within the emulsion droplets was observed with plane-polarized light in transmission mode on an Olympus IX 71 inverted fluorescence microscope with cross polarizers. Bright field images were taken using the same microscope. A 60× objective was used and images were captured with a color camera (FIGS. 9-12, 14, 15) and black and white camera (FIG. 13). Steady state fluorescent spectra were recorded using a Fluorolog Horiba fluorescence spectrophotometer using an excitation wavelength of 400 nm with a slit width at 2 nm.

Table 1 and Table 2 display properties of different types of bacteria (Gram +ve/−ve) and viruses (enveloped/non-enveloped). FIG. 15 depicts polarized light micrographs (crossed polars) of naked 5CB droplets with A/NWS/Tokyo/67 ($10^4$ pfu mL$^{-1}$).

TABLE 2

Properties of Enveloped and Non-Enveloped Viruses

| Properties | Enveloped virus A/NWS/Tokyo/67 | Non-enveloped virus M13 helper phage |
|---|---|---|
| Morphology | Bullet-shaped | Icosahedron |
| Membrane | Yes | No |
| Nucleic acid (wt %) | 1-4 | 10-15 |
| Lipid content (wt %) | 15-40 | 0 |
| Protein content (wt %) | 80-90 | 50-70 |

Example 7

Size-Dependent Ordering of Liquid Crystals Observed within Polymeric Capsules Synthesized with Sub-Micrometer Diameters It is widely appreciated that the supramolecular ordering of polymers, surfactants and liquid crystals (LCs) can be impacted by confinement. In many cases, however, these effects remain poorly understood. This is particularly true for LCs, where confinement-induced ordering in natural systems (e.g., containing DNA and proteins) underlies remarkable material properties such as the strength of spider silk, and confinement in synthetic systems influences the design of LC-based sensors, directed assembly of microscopic and nanoscopic objects, and the interactions of light with LCs. Although it is generally accepted that size-dependent ordering of LCs reflects a subtle competition between bulk and interfacial physicochemical factors, for the important and prototypical case of LC droplet systems, the absence of experimental approaches that permit precise variation of LC droplet size (in relevant size range) with rigorous control over interfacial chemistry, temperature and other key parameters of the system has prevented elucidation of the effects of confinement.

Here we report that it is possible to extend previously reported methods for preparation of aqueous dispersions of polymer-encapsulated LC droplets into the sub-micrometer range. The inventors use the capability to prepare micrometer and sub-micrometer LC droplets with precise control over size and interfacial chemistry to unmask size-dependent changes in LC ordering. A key aspect of the significance of our approach is that the inventors have been able to manipulate the size of the LC droplets without changing other parameters of the system. In particular, the inventors reveal that previous theoretical predictions of LC ordering in the limit of sub-micrometer droplet size are not realized experimentally, and the inventors propose an alternative physical picture to account for experimental observations. The inventors also report that the effects of size-dependent ordering can be exploited to manipulate LC ordering transitions that are triggered by the assembly of amphiphiles at the surfaces of the LC droplets, suggesting new principles for design of LC-based technologies, including chemical and biological sensors.

Although indirect observations reported in the past hint at size-dependent ordering within LC droplets, direct characterization of the effects of confinement on LCs droplets has not been reported. Furthermore, no prior theoretical study has unambiguously established the effect of droplet size on LC ordering. Order-of-magnitude thermodynamic arguments that describe competing bulk and surface effects have been proposed, and these lead to the widely held but untested prediction that the ordering of LC within small droplets will be uniform throughout the droplets.

Figure 16:
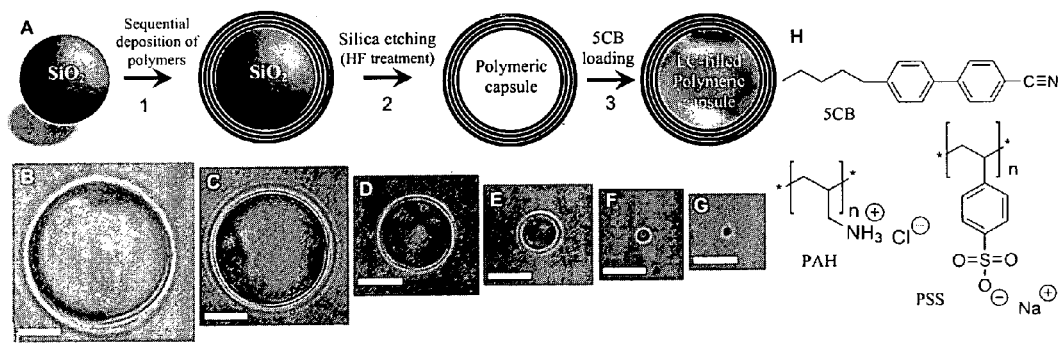
FIG. 16. (A) Schematic illustration of the preparation of LC droplets of predetermined sizes within polymeric multilayer shells. Polymeric shells were prepared by sequential deposition of PSS and PAH onto silica templates and subsequent etching of the silica. The resulting polymeric shells were filled with LC. (B-G) Bright-field micrographs of polymer-encapsulated 5CB droplets obtained using silica templates having diameters of 10±0.22 μm, 8±0.20 μm, 5±0.19 μm, 3±0.18 μm, 1±0.04 μm or 0.7±0.08 μm, respectively. The scale bars in all images correspond to 3 μm. (H) Structures of molecules used in this Example.
Figure 19:
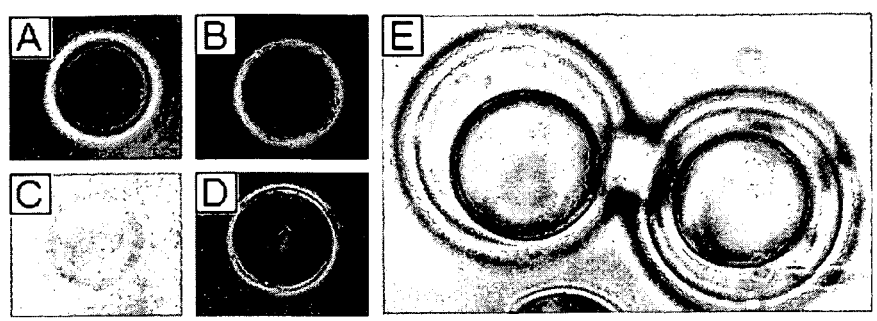
FIG. 19 (A-D). Optical micrographs that validate the steps involved in the template-based preparation of polymer-encapsulated LC droplets. (A) Bright-field micrograph of a 5.0±0.19 μm silica template particle, (B) fluorescence micrograph of the silica template particle in (A) coated with 6 layers of PSS/PAH (last layer is FITC-PAH), (C) bright-field micrograph of polymer capsule prepared by treatment of the polymer-coated particle in (B) with 5M HF (HF etches the silica core to create the hollow capsule), (D) bright-field micrograph of polymeric capsule in (C) that is completely filled with 5CB. For the purposes of comparison to (D), the bright-field micrograph in (E) shows polymer-capsules (obtained using 10±0.22 μm silica templates) that were deliberately under-filled with 5CB.

Previously, the inventors reported the preparation of aqueous dispersions of monodisperse droplets of the nematic LC 4'-pentyl-4-cyanobiphenyl (5CB) with diameters ranging from 3 to 10 μm that were wrapped in nanometer-thick, multilayered polymeric shells. Control over the LC droplet size was achieved by using monodispersed polymer shells, prepared by sequential adsorption of poly(styrene sulfonate) (PSS) and poly(allylamine hydrochloride) (PAH) onto sacrificial silica template particles (FIG. 16A) (see supporting FIG. 19). In this example, the inventors report that this synthetic procedure can be extended to smaller droplets than those reported previously and most importantly to sub-micrometer-sized droplets where size-dependent ordering of LC droplets is unmasked for the first time. FIGS. 16 B-G show bright-field images of 5CB-filled polymer shells with sizes ranging from 10.0±0.22 μm to 0.7±0.08 μm, demonstrating that precise control over LC droplet size extends from the micrometer-range into the sub-micrometer range. The droplets are encapsulated by identical polymeric layers thus giving rise to identical physicochemical interactions at the interfaces of the droplets. Because a large population of droplets (>$10^9$ droplets per mL) of the same size can be easily prepared, this approach enables definitive experimental observations (with high statistical confidence) regarding the size-dependence of LC ordering within the droplets. The inventors note that microfluidic-based approaches for preparation of monodisperse droplets are relatively low in throughput and have been limited so far to droplets with diameters larger than 3 μm. As discussed below, droplets with sizes greater than 3 μm do not show size-dependent ordering of LCs.

Figure 20:
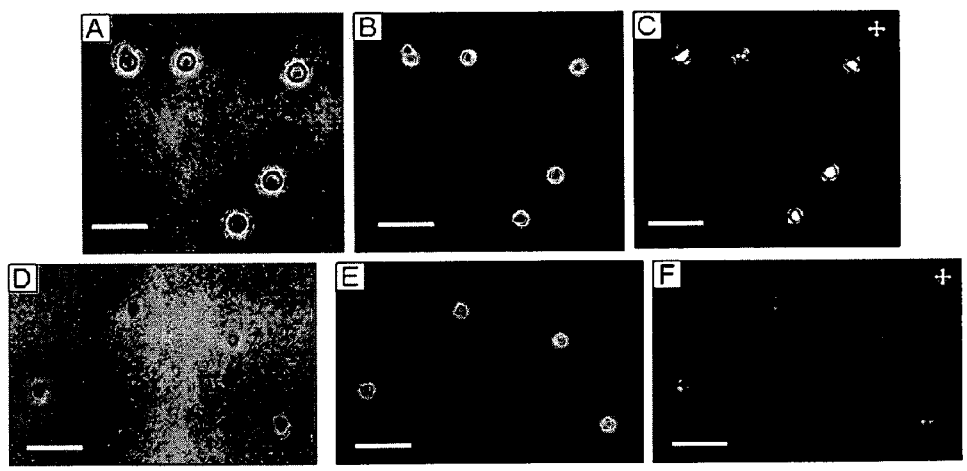
FIG. 20. Corresponding (A,D) bright-field, (B,E) fluorescent, and (C,F) polarized light micrographs of polymer-encapsulated 5CB droplets prepared by completely filling polymeric capsules synthesized using 1 μm (A-C) and 0.7 μm (D-F) silica templates. Scale bar for A-C is 3 μm and D-F is 2 μm.
Figure 21:
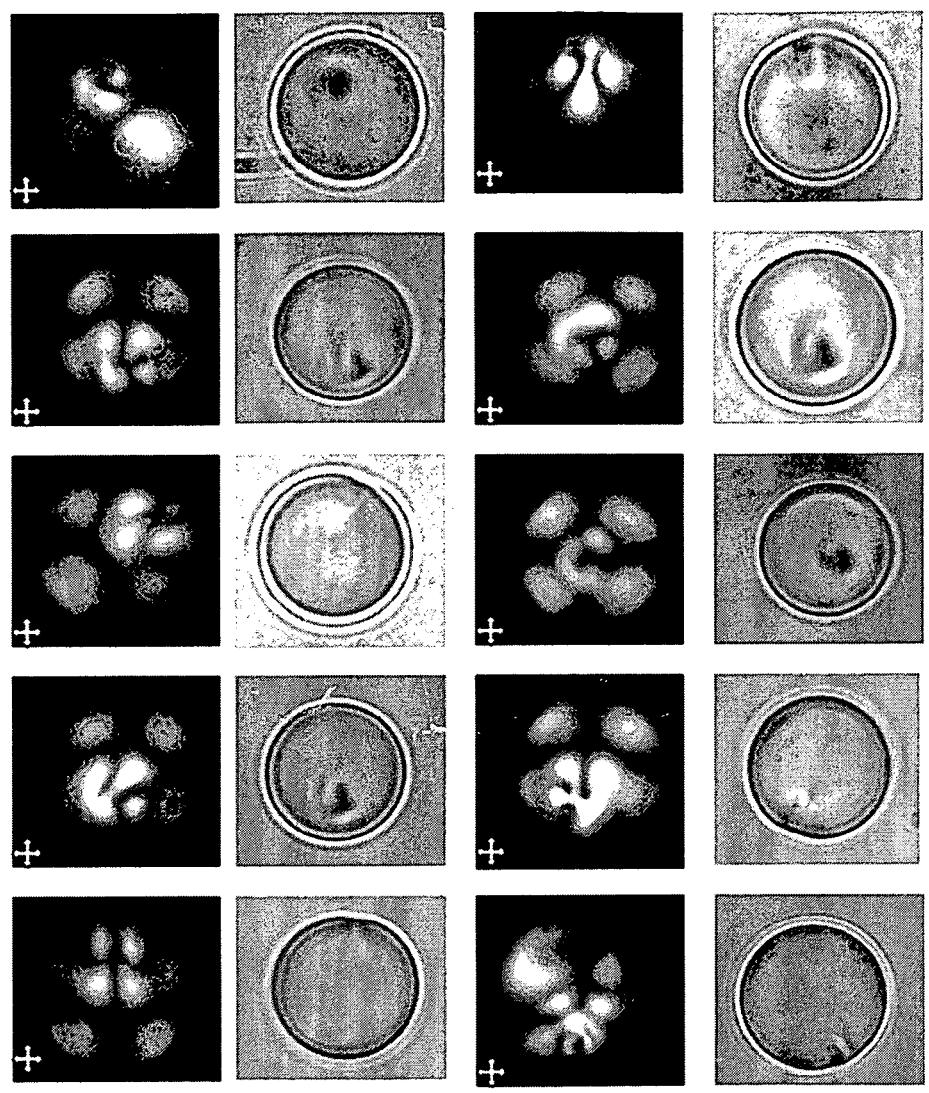
FIG. 21. Corresponding polarized and bright field micrographs of a single 8 μm-diameter, polymer-encapsulated LC droplet exhibiting preradial ordering (viewed with the LC symmetry axis at different angles with respect to the polarizer). The droplet was equilibrated with a bulk aqueous solution containing 0.6 mM SDS.

Thermodynamic arguments reported in the past for micrometer-sized LC droplets predict that the orientation-dependent interfacial energy scales with the square of the droplet radius (~$WR^2$ where $W$ is the anchoring strength coefficient) whereas the bulk elastic energy of the LC droplet scales linearly with droplet radius (~$KR$, where $K$ is the elastic constant of the LC). These thermodynamic considerations lead to the prediction that LC droplets having $R \ll K/W$ will avoid spatial variation of the orientation of the LC within the droplet ($n(r)$=constant, where n is so-called director of the LC) (as shown in FIG. 17B). To test this prediction, the inventors synthesized LC droplets of different sizes, but with identical surface chemistry, by using the above described procedure (FIG. 16). FIGS. 17C and D show polarized light and bright-field micrographs, respectively, that permit identification of the ordering of LC within droplets prepared using the 8.0±0.2 μm silica template. These micrographs are consistent with two point defects at the poles of the droplet, referred to as a bipolar director configuration (FIG. 17E). The inventors also observed LC-filled shells prepared from templates with diameters of 10±0.22 μm, 5.0±0.19 μm and 3.0±0.18 μm to exhibit an optical appearance identical to the 8.0±0.2 μm LC droplet, thus consistent with the presence of the two boojums (data not shown). In contrast to the larger LC droplets, bright-field images of droplets with diameters of 1.0±0.04 μm (FIGS. 17G and I) exhibited only one point defect. The apparent location of the point defect ranged from the droplet center (FIG. 17G) to the droplet edge (FIG. 17I), with the majority (90%) lying between these limits (see supporting FIG. 20A). When combined with the polarized light micrographs in FIGS. 17F and H, these bright field images lead the inventors to conclude that the LC ordering within the 1 μm LC droplet corresponds to single point defect lying on the droplet surface (FIG. 17J; the apparent locations of the defects in FIGS. 17G and I depend upon the angles at which the droplets are viewed). This ordering of the LC is described as a "preradial". Identification of the preradial ordering of the 1 μm-sized LC droplets was further assisted by the preradial ordering also observed with bigger LC droplets decorated with the anionic surfactant, sodium dodecyl sulfate (SDS) (see supporting FIG. 21). Polarized light micrographs of the smallest droplets used in the inventors' study (diameters of 0.70±0.08 μm) reveal a third type of optical signature (FIG. 17K) corresponding to a radial director configuration (FIG. 17M). They note that the bright-field image of the 0.70±0.08 μm droplet in FIG. 17L does not show a point defect at the droplet center due to the far-field resolution limits of optical microscopy (see supporting FIG. 20). Although the synthesis of droplets smaller than 0.7 μm is within the capabilities of the methods reported above, with far-field optical microscopy, it is not possible to characterize the ordering of LC within droplets with sizes less than 0.7 μm.

Figure 17:
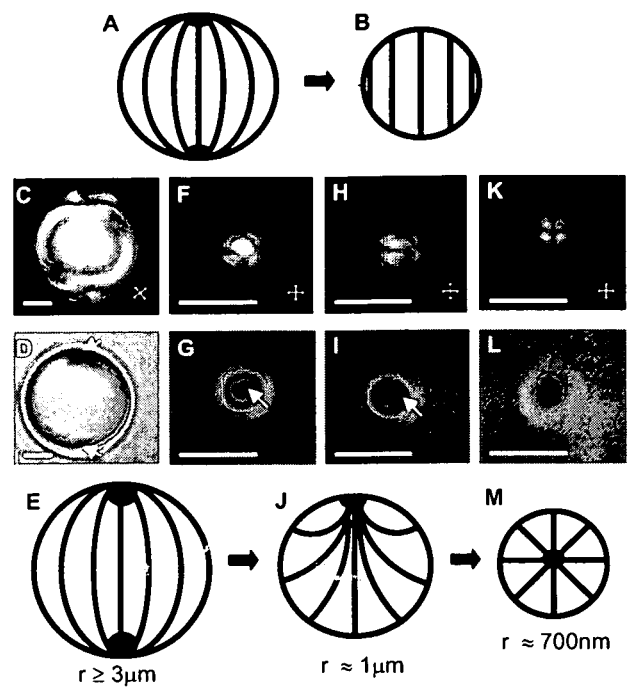
FIG. 17. Schematic illustrations in (A) and (B) shows, respectively, the bipolar and homogeneous director configurations. Polarized (C, F, H, K) and bright-field (D, G, I, L) optical micrographs of polymer-encapsulated 5CB droplets with (C, D) diameters of 8.0±0.2 μm and bipolar LC ordering, (F-I) diameters of 1.0±0.2 μm and preradial LC ordering (F and G show the head-on views of the preradial ordering whereas H and I show side views), and (K, L) diameters of 0.70±0.08 μm and radial LC ordering. Point defects in the LCs are indicated by white arrows. Cartoons in E, J and M show bipolar, preradial and radial ordering of the LC droplets, respectively. The scale bars are 2 μm for C-I and 1 μm for K, L.

The results above reveal for the first time that the ordering of LCs within droplets with constant interfacial chemistry changes with decreasing droplet size from bipolar (FIG. 17E) to preradial (FIG. 17J) and then to a radial ordering (FIG. 17M). The observation of bipolar ordering in the limit of large droplet size indicates that the preferred alignment (easy axis) of the LC at the surface of each droplet is parallel to the droplet surface. Our experimental observation of radial ordering in the smallest LC droplets is, therefore, surprising in light of the above-described prediction of a uniform LC orientation within small droplets (FIG. 17 B). To provide insight into the above experimental observations, the inventors considered the possible effects of saddle-splay and splay-bend elastic energies, both of which were ignored in the past thermodynamic arguments. The energetic effects of saddle-splay ($K_{24}$) and splay-bend ($K_{13}$) elasticity can be described by the Frank-Oseen elastic energy density and minimization of this energy density (see supporting information below) leads the inventors to conclude that radial ordering of a LC droplet (FIG. 17M) is stable relative to uniform ordering (FIG. 17B) when the following constraint is satisfied, $K_{11}+K_{13}+WR/6<K_{24}/2$, where $K_{11}$ is splay elastic constant of LC. This relationship predicts that for droplets with $R<6K^*/W$ (where $K^*=K_{24}/2-K_{13}-K_{11}$), uniform ordering will not be observed (relative to radial ordering). Estimates of $K_{24}$ and $K_{13}$ for 5CB are $K_{24} \approx 3.1 K_{11}$ and $K_{13} \approx -0.2 K_{11}$, leading to $K^* \approx 0.75 K_{11}$, and the conclusion that LC droplets with radial ordering are stable in the limit of small LC droplet size, as seen in the inventors experiments. The inventors emphasize that their experiments and refined thermodynamic argument indicate that uniform ordering of LC within droplets should not be expected in the limit of small droplet size (provided continuum descriptions of the LC remain valid). More broadly, by tuning size at constant interfacial chemistry, the results demonstrate the subtle balance between bulk and surface energetics that controls the ordering of LC within droplets.

Figure 18:
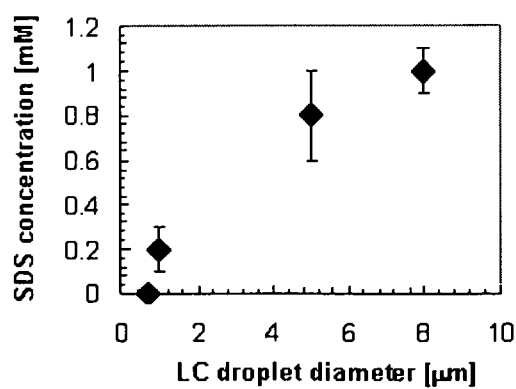
FIG. 18. Size-dependent response of polymer-encapsulated LC droplets to concentration of model analyte (SDS). The SDS concentration required to cause radial ordering within the LC droplet is plotted as a function of droplet size.

In addition to allowing size-dependent ordering to be identified within LC droplets with precisely controlled interfacial chemistry, the experimental system described above also enables ordering induced by changes in interfacial chemistry to be studied in LC systems of well-defined size. Here the inventors focus on LC ordering transitions induced by SDS, as past studies have demonstrated that SDS can permeate through the polymer shell to change the orientation of the LC from parallel to perpendicular. They also note here that prior reports have established that a range of adsorbates (e.g., lipids, polymers and proteins) can trigger changes in the ordering of LCs in contact with aqueous solutions. To determine if control of the size of LC droplets might provide the basis of a simple and general method to tune LC ordering transitions triggered by interfacial adsorbates, they investigated the bulk concentration of SDS needed to cause radial ordering of LC droplets as a function of droplet size. FIG. 18 reveals that the concentration of SDS that triggers radial ordering of the LC decreases continuously with decreasing droplet size. Other results (not shown) revealed that for a given concentration of SDS, LC droplets exhibit size-dependent ordering. Overall, these results lead the inventors to conclude that control over LC droplet size in the micrometer-to-sub-micrometer range does allow the ordering response of LCs to interfacial adsorbates to be tuned, and that it holds particular promise as a means to control the sensitivity and dynamic range of LC-based chemical and biological sensors.

In conclusion, this study establishes the feasibility of synthesizing polymer-encapsulated LC droplets with sizes in the sub-micrometer range. The capability to prepare droplets in this size range with precise control over interfacial chemistry is significant because it is in the micrometer-to-sub-micrometer size range that size-dependent ordering of LCs is observed. Observations of size-dependent ordering of LC droplets reveal that previous theoretical predictions of uniform LC orientations in the limit of small droplet size are not realized experimentally. More broadly, the experimental system reported in this example resolves ambiguities in prior experimental observations regarding the effects of size and interfacial chemistry on the order within LC droplets, and it provides access to experimental data sets for developing a more complete description of the effects of confinement on the ordering of LCs.

Supporting Information. Materials and Methods. Materials. Poly(sodium-4-styrene sulfonate) (PSS, Mw 70 kDa), poly(allylamine hydrochloride) (PAH, Mw 70 kDa), sodium dodecyl sulfate (SDS), and 3-aminopropyltriethoxysilane (APTS) were purchased from Sigma-Aldrich and used without further purification. Fluorescein isothiocyanate-labeled PAH (FITC-PAH, Mw 70 kDa) was prepared as described previously. Nematic 4'-pentyl-4-cyanobiphenyl (5CB) was purchased from EMD Chemicals (Hawthorne, N.Y.). Monodisperse silica template particles with diameters of $0.7\pm0.08$ μm, $1\pm0.04$ μm, $3\pm0.18$ μm, $5\pm0.19$ μm, $8\pm0.2$ μm, $10\pm0.22$ μm were purchased from Microparticles (Berlin, Germany). Hydrofluoric acid (HF) was purchased from Sigma-Aldrich. Deionization of a distilled water source was performed with a Milli-Q system (Millipore, Bedford, Mass.) to give water with a resistivity of 18.2 MΩ·cm.

Filling of polymeric capsules with LC. The steps used to prepare the LC droplets with defined sizes and interfacial chemistries are shown in FIG. 1A. The procedure was adapted with minor modification (see below) from that described in Jang, S. Sivakumar, J. K. Gupta, N. L. Abbott, F. Caruso, Chemistry of Materials 2008, 20, 2063.

Coating of silica templates with multilayers of polymers: Monodisperse silica template particles with sizes of 0.7, 1, 3, 5, 8 and 10 μm were reacted with 3-aminopropyltriethoxysilane (APTS) to create particles with a net positive surface charge according to the procedure described previously [Y. J. Wang, F. Caruso, Chemistry of Materials 2006, 18, 4089.]. Next, the APTS-modified silica microspheres were coated with 6 layers of PSS/PAH (2 mg/mL solution of each with 0.5 M NaCl), with PSS and PAH being the first and outer layers, respectively. An aqueous solution of 0.5 M NaCl was used for three intermediate rinsings. To avoid particle aggregation (particularly for 0.7 μm diameter particles), the high concentration of polyelectrolyte solution (2 mg/mL) was found to be necessary. For multilayer coating, 2 ml of polyelectrolyte solution was used to coat 20 mg of particles. To permit imaging by fluorescence microscopy, one of the PAH layers was FITC-labeled PAH.

Preparation of Polymeric Capsules: the Polymer-Coated Silica Template particles thus obtained were treated twice with 5 M HF to etch the silica cores (Extreme care should be taken while handling HF). The resulting polymeric capsules were washed five times with water and three times with ethanol. After each wash, the capsules were concentrated by centrifugation and the supernatant was removed. In an ethanol environment, the thickness of the polymeric shells shrink by 5% of the original thickness in water.

Filling of polymeric capsules with LC: The pellet of ethanol-filled polymeric capsules obtained after the last washing step (suspended in a small amount of ethanol ~5 μL) was contacted with 100 μL of 5CB and the mixture was incubated for 24 h at 22° C. The mixture of ethanol and 5CB formed an isotropic phase that infiltrated through the walls of the polymeric capsules. In contrast to our previously reported procedure [S. Sivakumar, J. K. Gupta, N. L. Abbott, F. Caruso, Chemistry of Materials 2008, 20, 2063], the inventors next removed the ethanol from the mixture by application of a vacuum (30 in-Hg) for 2 h in a vacuum oven at room temperature. Upon removal of the ethanol, the 5CB transformed into its nematic phase, and the system was allowed to equilibrate for an additional 24 h. In contrast to previously reported procedures the inventors removed excess 5CB from outside of the polymeric capsules by contacting the capsules with water and centrifuging the mixture. Theye observed this procedure to result in the formation of a stratified layer of 5CB-filled polymeric capsules that were located between the bulk 5CB phase and bulk aqueous phase. The LC-filled capsules were extracted from the interfacial layer using a Pasteur pipette and dispersed in water. This procedure resulted in a high yield of monodisperse LC droplets.

Changing interfacial chemistry by surfactant adsorption: To obtain surfactant-decorated LC droplets, less than $10^5$ polymer-coated LC droplets were equilibrated with 2 mL of aqueous solution that contained a predefined concentration (ranging from 0 to 1 mM) of the surfactant SDS. The ratio of surfactant present in solution to that adsorbed to the interface of the LC droplets was kept to approximately 1000 to avoid depletion of surfactant in the aqueous phase because of adsorption to the aqueous-LC interface.

Polarized, bright-field and fluorescent images of LC-filled polymeric capsules were taken using an Olympus IX-71 inverted microscope at 100× magnification and 1.6 optical zoom. Images were obtained by placing the emulsion on a cover slip.

Interpretation of Optical Images. (1) Bipolar: In a bipolar configuration, the director (local alignment of LC) follows the contour of the surface of the droplet, connecting the two diametrically opposed point defects called boojums at the poles of the LC droplets (FIG. 17E). The presence of two point defects as observed in the bright-field image in FIG. 17D (indicated by white arrows) and the corresponding characteristic polarized image (FIG. 17C) confirms the bipolar director configuration in 8 µm polymer-encapsulated 5CB droplets (see P. S. Drzaic, Liquid Crystal Dispersions, World Scientific Publishing Company, Singapore, 1995 for a detailed discussion of the optical signatures of bipolar ordering). The absence of twist deformation within the droplets is consistent with $K_{11} \leq K_{22} + 0.431 K_{33}$ [$K_{11}$, $K_{22}$ and $K_{33}$ are the splay, twist and bend elastic constants of the LC, with values for 5CB of 6.4 pN, 4 pN and 10.1 pN, respectively] for 5CB.

(2) Preradial: In a preradial director configuration, the LC droplet possesses one point defect lying on the droplet surface (as shown in the cartoon in FIG. 17J). The inventors interpretation of the polarized light micrographs of the 1 µm LC droplets (FIG. 17 F-I) was aided by complementary studies of preradial configurations in larger droplets (see FIG. 21). Comparison of images in FIG. 21 to FIGS. 17G and 17I leads us to conclude that FIG. 17G is a head-on view of the preradial director configuration within the 1 µm LC droplet, while FIG. 17I corresponds to side view of the preradial configuration.

(3) Radial: In a radial director configuration, the LC droplet has one point defect located at the center of the droplet. The director radiates from the center and is normal to the interface. The radial droplet has the most symmetric director configuration and the optical appearance of the droplet is invariant when viewed at differing angles under a polarized light microscope. Observation of the characteristic (crossed) optical texture in an entire population of 0.7 µm-sized droplets confirmed the presence of the radial defect in FIGS. 17K and L (and eliminated the possibility of a head-on view of an axial director configuration).

(5) Homogeneous director profile: In a LC droplet with a homogenous director profile (FIG. 17B), there is no elastic distortion of the LC (no splay, bend, twist, saddle splay or splay-bend). To the inventors knowledge, no experimental study has reported optical micrographs of a LC droplet with a homogeneous director profile.

Derivation of equation (2). To evaluate the relative stability of a LC droplet with radial ordering as compared to a LC droplet that possesses a homogeneous director profile, the inventors estimated the magnitude of the elastic and surface energy terms in Frank-Oseen elastic energy density equation (Eq. 1), $$F = \frac{1}{2}[K_{11}(\nabla \cdot n)^2 + K_{22}(n \cdot \nabla \times n)^2 + K_{33}(n \times \nabla \times n)^2 - K_{24}\nabla \cdot \{n(\nabla \cdot n) + n \times \nabla \times n\}] + K_{13}\nabla \cdot [n(\nabla \cdot n)] + \frac{1}{2}W\sin^2(\theta - \theta_e) \quad (1)$$

to obtain the following inequality;

$$\underbrace{8\pi R K_{11}}_{Splay} - \underbrace{4\pi R K_{24}}_{Saddle-splay} + \underbrace{8\pi R K_{13}}_{Splay-bend} + \underbrace{2\pi R^2 W}_{Surface\ anchoring} < \quad (2)$$

Droplet with radial configuration

-continued $$\underbrace{\frac{2}{3}\pi R^2 W}_{Surface\ anchoring}$$

Droplet with homogeneous director profile

Upon simplification, Eq. 2 reduces to $$K_{11} + K_{13} + \frac{WR}{6} < \frac{K_{24}}{2} \quad (3)$$

Example 8

Figure 22:
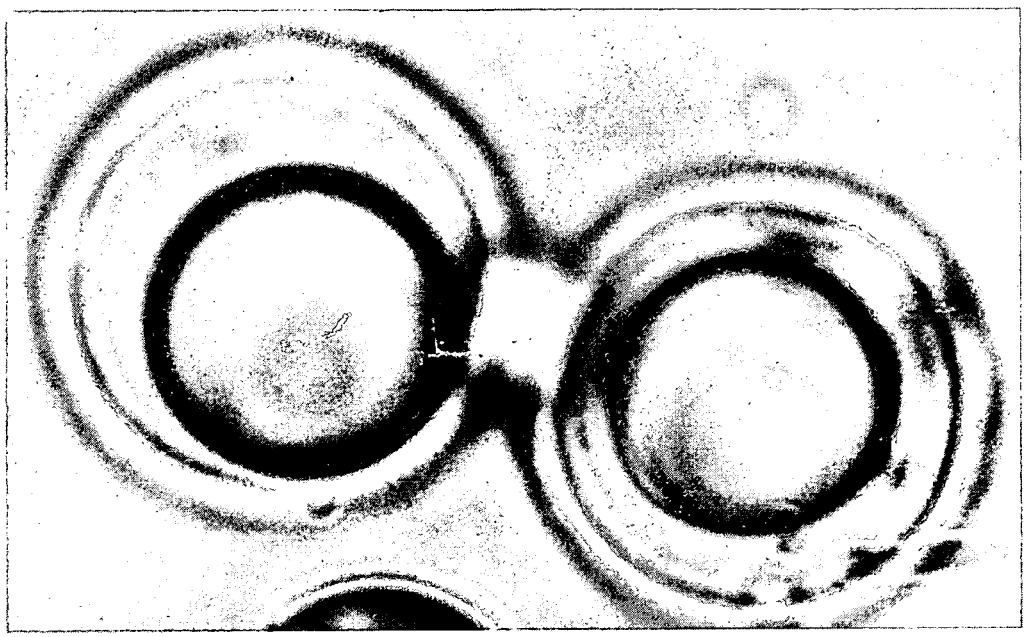
FIG. 22. Micrographs show polymer-capsules (obtained using 10±0.22 μm silica templates) that were deliberately under-filled with 5CB to obtain polymeric capsules confining two phases (oil and water).

Partial filling of polymeric capsules with liquid crystal. In this example, a spherical 10 µm silica template was used to prepare polymeric capsules as described in example 2. The polymeric capsules were filled partially (using the procedure as described in the above examples for completely filling the capsules) with the liquid crystal 5CB by incubating the capsules with 5CB only for 1 hr. The bright-field micrograph in FIG. 22 shows polymer-capsules (obtained using 10±0.22 µm silica templates) that were deliberately under-filled with 5CB to obtain polymeric capsules confining two phases (oil and water).

Example 9

Figure 23:
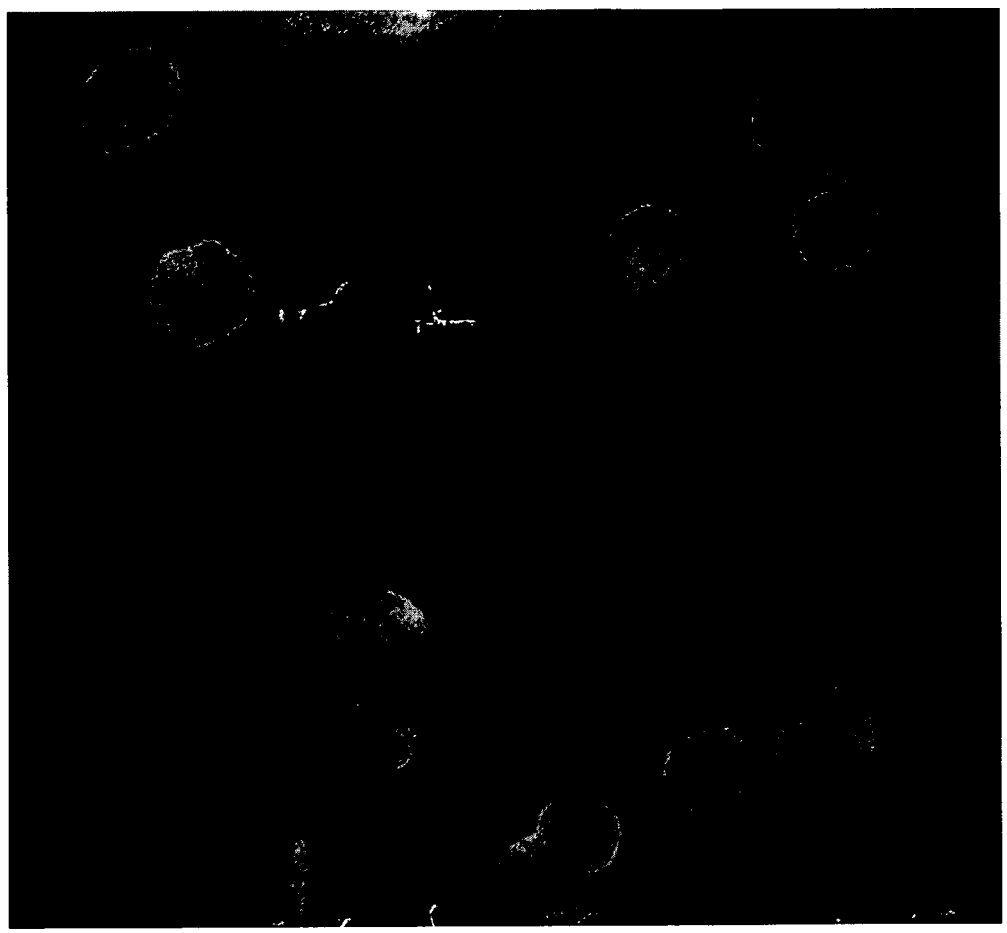
FIG. 23. Micrographs show fluorescent image of non-spherical polymeric capsules. Non-spherical (octahedral) polymeric capsules were then filled with the liquid crystal 5CB. The capsules were filled using the procedure similar to the one used for filling 5 μm-sized spherical polymeric capsules.
Figure 24:
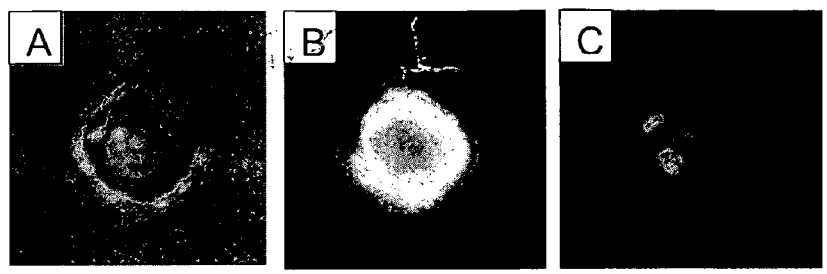
FIG. 24. Micrographs show (A) bright-field, (B) fluorescent and (C) polarized images of a non-spherical capsule filled with 5CB.

Non-spherical capsules. In this example, non-spherical (octahedral) polymeric capsules were prepared from an octahedral silica template particle (5 µm) synthesized in the lab using the procedure described elsewhere (Guan et al., Journal of American Chemical Society 2000, 122, 5660). The capsules were prepared using a procedure similar to the one used for spherical templates. FIG. 23 shows fluorescent image of non-spherical polymeric capsules. Non-spherical (octahedral) polymeric capsules were then filled with the liquid crystal 5CB. The capsules were filled using the procedure similar to the one used for filling 5 µm-sized spherical polymeric capsules. FIG. 24 shows (A) bright-field, (B) fluorescent and (C) polarized images of a non-spherical capsule filled with 5CB.

Example 10

Figure 25:
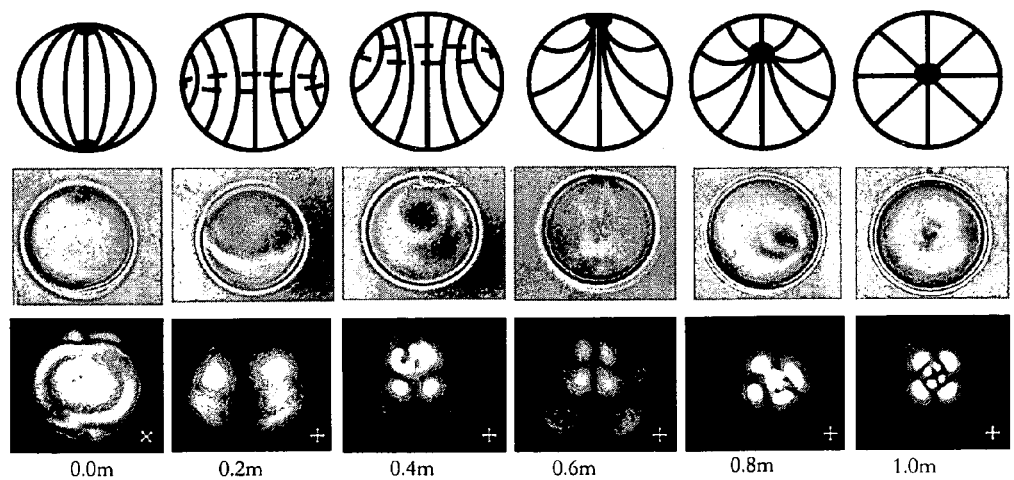
FIG. 25. The top row in this figure shows schematic illustrations of the topological order within each LC droplet, and the middle and bottom rows, respectively, show the corresponding bright-field and polarized light micrographs of the 5CB droplets.

Surface-driven ordering transitions within LC droplets of fixed size. In this example, polymer encapsulated 5CB droplets of 8.0 µm size were prepared using the procedure described in example 3. The change in boundary condition at the surface of the LC droplet (from tangential to perpendicular) was achieved by equilibrating 8.0 µm-diameter, polymer-encapsulated 5CB droplets with aqueous solutions containing SDS at concentrations that ranged from 0 to 1 mM. To obtain surfactant-decorated LC droplets, less than $10^5$ polymer-coated LC droplets were equilibrated with 2 mL of aqueous solution that contained a predefined concentration (ranging from 0 to 1 mM) of the surfactant SDS. The ratio of surfactant present in solution to that adsorbed to the interface of the LC droplets was kept to approximately 1000 to avoid depletion of surfactant in the aqueous phase because of adsorption to the aqueous-LC interface. The top row in FIG. 25 shows schematic illustrations of the topological order within each LC droplet, and the middle and bottom rows, respectively, show the corresponding bright-field and polarized light micrographs of the 5CB droplets.

Example 11

Figure 26:
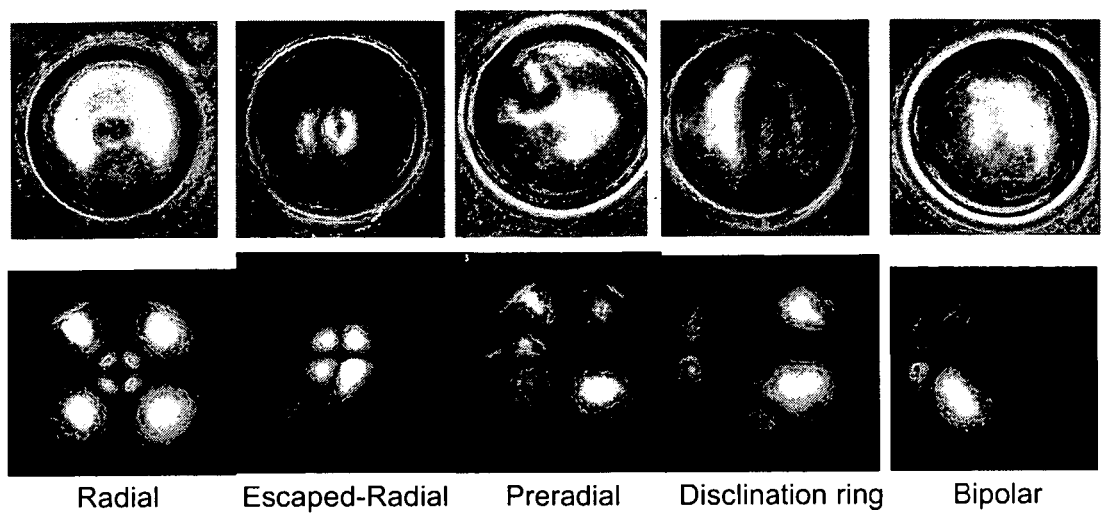
FIG. 26. Micrograph shows the changes in the optical appearance of the LC droplets when kept in contact with 1 nM $PLA_2$ for 1 hr.

Reporting the activity of enzyme PLA. In this example, naked 5CB droplets of 8.0 μm size were prepared as described in example 2 and 3 and were dispersed in TBS buffer of pH 8.9. The droplets were contacted with 700 μM concentration of phospholipid L-dipalmitoyl phosphatidylcholine (L-DLPC) for 1 hr and then rinsed three times with TBS buffer to remove all unadsorbed lipid. The lipid-saturated droplets were then contacted with 1 nM concentration of enzyme phospholipase $A_2$ ($PLA_2$). FIG. 26 shows the changes in the optical appearance of the LC droplets when kept in contact with 1 nM $PLA_2$ for 1 hr.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

What is claimed is:

1. A method for providing naked oil emulsion droplets, the method comprising:
   (a) preparing multilayer capsules by:
      (i) layer-by-layer (LbL) coating of sacrificial particles with one or more types of macromolecular assembly materials to yield sacrificial particles having a pH sensitive semipermeable multilayer coating sensitive to disassembling at a certain pH; and
      (ii) etching the sacrificial particles having the pH sensitive semipermeable multilayer coating to remove the sacrificial particle thereby yielding the multilayer capsules, wherein the multilayer capsules have an internal cavity obtained by removal of the sacrificial particle and the pH sensitive semipermeable multilayer coating enclosing the internal cavity;
   (b) infiltrating oil from outside of the multilayer capsules through the pH sensitive semipermeable multilayer coating into the internal cavity of the multilayer capsules to provide pH sensitive semipermeable multilayer-coated oil droplets; and
   (c) disassembling the pH sensitive semipermeable multilayer-coating of said pH sensitive semipermeable multilayer-coated oil droplets by exposing to a solution having the pH at which the pH sensitive semipermeable multilayer coating is sensitive to disassembling; whereby the naked oil emulsion droplets are provided.

2. The method according to claim 1, wherein the macromolecular assembly materials include at least one polycation and one polyanion that yield multilayer-coated sacrificial particles having alternating layers of said polycation and polyanion in the LbL coating step.

3. The method according to claim 1, wherein the macromolecular assembly materials include at least two non-ionic polymers that yield multilayer-coated sacrificial particles having alternating layers of said non-ionic polymers in the LbL coating step.

4. The method according to claim 1, wherein the diameter of the multilayer capsules is predetermined and ranges from about 10 nm to about 10 mm.

5. The method according to claim 1, wherein said naked oil emulsion droplets are naked monodisperse oil emulsion droplets of a predetermined diameter of from about 10 nm to about 10 mm.

6. The method according to claim 1, wherein said naked oil emulsion droplets are naked monodisperse liquid crystal emulsion droplets.

7. The method according to claim 6, wherein the naked monodisperse liquid crystal emulsion droplets have a uniform predetermined diameter from about 0.1 μm to about 10 μm.

8. The method according to claim 6, wherein said naked monodisperse liquid crystal emulsion droplets have a granulomeric distribution of about 30% or less.

9. The method according to claim 8, wherein said naked monodisperse liquid crystal emulsion droplets have a granulomeric distribution of about 10% or less.

10. The method according to claim 1, wherein said naked oil emulsion droplets are monodisperse and have a granulomeric distribution of about 10% or less.

* * * * *